United States Patent
Emmons et al.

(10) Patent No.: US 7,618,650 B2
(45) Date of Patent: *Nov. 17, 2009

(54) COMBINATION OF A HYPNOTIC AGENT AND SUBSTITUTED BIS ARYL AND HETEROARYL COMPOUND AND THERAPEUTIC APPLICATION THEREOF

(75) Inventors: Gary Emmons, Washington, NJ (US); Sathapana Kongsamut, Madison, NJ (US); Craig N. Karson, Wayne, PA (US); Corrine M. Legoff, Montclair, NJ (US)

(73) Assignee: Aventis Pharmaceuticals Inc, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/027,022

(22) Filed: Feb. 6, 2008

(65) Prior Publication Data

US 2008/0138413 A1  Jun. 12, 2008

Related U.S. Application Data

(63) Continuation of application No. PCT/US2006/032027, filed on Aug. 16, 2006.

(60) Provisional application No. 60/709,655, filed on Aug. 19, 2005.

(51) Int. Cl.
| | |
|---|---|
| *A61K 31/5513* | (2006.01) |
| *A61K 31/519* | (2006.01) |
| *A61K 31/52* | (2006.01) |
| *A61K 31/503* | (2006.01) |
| *A61K 31/4745* | (2006.01) |
| *A61K 31/425* | (2006.01) |
| *A61K 31/405* | (2006.01) |
| *A61K 9/22* | (2006.01) |

(52) U.S. Cl. .................. 424/468; 514/221; 514/419; 514/263.1; 514/248; 514/300; 514/373; 514/260.1; 514/265.1; 514/301; 514/302; 514/303

(58) Field of Classification Search .................. None
See application file for complete search history.

(56) References Cited

U.S. PATENT DOCUMENTS

| | | | | |
|---|---|---|---|---|
| 6,218,547 | B1* | 4/2001 | Teuber et al. | 548/304.4 |
| 2002/0077332 | A1* | 6/2002 | Aronhime et al. | 514/300 |
| 2004/0258750 | A1* | 12/2004 | Alaux et al. | 424/464 |
| 2007/0265309 | A1* | 11/2007 | Eastwood et al. | 514/320 |

FOREIGN PATENT DOCUMENTS

WO    WO 2006/086705    8/2006

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*

* cited by examiner

*Primary Examiner*—Brian-Yong S Kwon
*Assistant Examiner*—Bong-Sook Baek
(74) *Attorney, Agent, or Firm*—Balaram Gupta

(57) ABSTRACT

The invention concerns the combination of a short-acting hypnotic agent and a compound of formula (I):

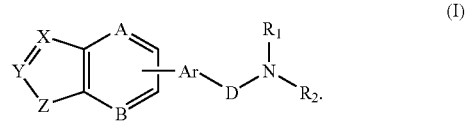

Wherein X, Y, Z, A, B, D, Ar, $R_1$ and $R_2$ are as defined herein. The combination of this invention is useful in treating a variety of sleep disorders.

11 Claims, No Drawings

COMBINATION OF A HYPNOTIC AGENT AND SUBSTITUTED BIS ARYL AND HETEROARYL COMPOUND AND THERAPEUTIC APPLICATION THEREOF

CROSS REFERENCE TO RELATED APPLICATIONS

This application is a continuation of International application No. PCT/US2006/032,027, filed Aug. 16, 2006, which is incorporated herein by reference in its entirety; which claims the benefit of priority of U.S. Provisional Application No. 60/709,655, filed Aug. 19, 2005.

BACKGROUND OF THE INVENTION

1. Field of the Invention

The present invention relates to a combination of at least one hypnotic agent with at least one substituted bis aryl and heteroaryl compound. More specifically, the present invention relates to a combination containing at least one hypnotic agent with at least one compound selected from a series of dialkylamino, piperidinyl or piperazinyl substituted bis aryl and heteroaryl derivatives, which are selective serotonin, $5HT_{2A}$, antagonists. The combination of this invention is useful in the treatment of a variety of sleep disorders.

2. Description of the Art

Chronic insomnia among adults in the United States has been estimated to be present in ten percent of the adult population, and the annual cost for its treatment is estimated at $10.9 billion. JAMA 1997; 278:2170-2177 at 2170. Chronic insomniacs report elevated levels of stress, anxiety, depression and medical illnesses. The most common class of medications for treating insomnia are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4-6 weeks because of concerns raised over drug misuse, dependency, withdrawal and rebound insomnia. JAMA 1997; 278:2170-2177 at 2170. Therefore, it is desirable to have a pharmacological agent for the treatment of insomnia which is more effective and/or has fewer side effects than those currently used.

The prevalence of obstructive sleep apnea is estimated to be approximately 1-10% in the adult population, but may be higher in elderly individuals; Diagnostic and Statistical Manual of Mental Disorders $4^{th}$ ed., American Psychiatric Association, Washington D.C. (1994). Preliminary evidence suggests that having obstructive sleep apnea may contribute to increased susceptibility to cardiovascular complications such as hypertension, cardiac arrhythmias, stroke, and myocardial infarction. Excessive daytime sleepiness is also a major complication.

Currently, the therapies used to treat obstructive sleep apnea include weight loss for the obese patient, Nasal-continuous positive Airway Pressure (a facemask used at night which produces a positive pressure within the upper airway), pharyngeal surgery and the administration of a variety of pharmacologic agents which have not been proven to be entirely successful. Chest 109 (5):1346-1358 (May 1996) entitled "Treatment of Obstructive Sleep Apnea", a Review, hereby incorporated by reference. These agents include acetazolamide, medroxyprogesterone, opioid antagonists, nicotine, angiotensin-converting enzyme inhibitors and psychotropic agents (including those that prevent the reuptake of biogenic amines such as norepinephrine, dopamine and serotonin). Id. at 1353. Many of these pharmacological agents used also have a ventilatory depressant action (such as benzodiazepines) or other side effects such as urinary hesitancy and/or impotence in men (protriptyline) so that a new agent with fewer side effects is needed for the treatment of obstructive sleep apnea. Even though serotonin is a sleep-inducing agent and may be a ventilatory stimulant (Id. at 1354), $5HT_{2A}$ receptor antagonists have been found useful in treating obstructive sleep apnea. See also Am. J. Respir Crit. Care Med (153) pp 776-786 (1996) where serotonin antagonists exacerbated sleep apnea produced in English bulldogs. But compare, Journal of Physiology (466) pp 367-382 (1993), where it is postulated that an excess of serotonin due to dysfunction of the serotonin biosynthesis mechanisms might set up conditions which favor obstructive apneas; European Journal of Pharmacology (259):71-74 (1994) further work on rat model with $5HT_2$ antagonist.

EP 1 262 197 discloses a method of treating sleep disorders including sleep apnea by administering to a patient in need of such a treatment a $5HT_{1A}$ antagonist or an alpha-2-adrenergic antagonist in combination with an antidepressant such as serotonin reuptake inhibitor (SRI). Such a combination exhibits an improvement in efficacy.

U.S. Pat. No. 6,143,792 discloses that a specific $5HT_{2A}$ receptor antagonist is useful in the treatment of the sleep apnea syndrome. Similarly, U.S. Pat. No. 6,576,670 discloses that a specific $5HT_{2A}$ and $5HT_{2A/C}$ receptor antagonist is useful in the treatment of snoring and upper airway high resistance syndrome.

U.S. Pat. No. 6,277,864 discloses that a specific $5HT_{2A}$ receptor antagonist is useful in the treatment of a variety of sleep disorders.

A certain number of hypnotic agents, having various modes and acting duration, have also been developed over the years. For instance, a class of hypnotic agents have been developed which are long acting ones. Also, a class of short-acting hypnotic agents has also been developed. Generally, a short acting hypnotic agent acts mainly as a sleep inducer, i.e., the entry time into the sleep phase.

An example of a short acting hypnotic agent include without any limitation, zolpidem, which acts as a modulator of the GABA-A receptors. Zolpidem belongs to the imidazopyridine class and is administered orally in the form of an immediate-release tablet or in a galenic form allowing a delayed release. Zolpidem acts quickly, and is well absorbed with a 70% bioavailability. The average dosage, between 5 and 10 mg in a conventional formulation, induces a maximum plasma concentration which is reached between 0.5 and 3 hours of administration, the half life is short, with an average value of about 2.4 hours and an acting time of up to 6 hours.

Other examples of a short-acting hypnotic agent include without any limitation zaleplon, which belongs to the pyrazolopyrimidine class, zopiclone, eszopiclone, which belong to the cyclopyrrolone class, as well as their derivatives. Various other short acting hypnotic agents have also been developed including phenothiazines and benzodiazepines. Specific compounds belonging to these therapeutic classes include for example triazolam, brotizolam or alimemazine.

Long-acting hypnotic agents and/or sleep aids have also been developed. In the following it is understood that a long-acting hypnotic agent is referred to a compound or agent that is mainly a sleep inducer but may also be capable of improving sleep quality and/or maintenance in a patient. The "sleep aid" is a compound or agent that is mainly used to improve sleep quality and/or sleep maintenance in a patient, in particular the deep sleep phases. One such example of a sleep aid is an inhibitor of the 5HT2A receptors that acts without blockage of the dopamine, such as compounds of formula (I) as described herein.

Other long-acting hypnotic agents are, for example, temazepam, clonazepam, gaboxadol and pregabaline, a modulator of calcium ion, as well as their derivatives.

The hypnotic agents and/or the sleep aids described above improve sleep disorders, in particular, insomnia. However, whereas the short-acting hypnotic agents act mainly on the sleep-entry phase, the long-acting hypnotic agents act mainly on the sleep-entry phase but may also have a sleep maintenance component and sleep aids act rather on the deep-sleep phase, thus help to improve the overall quality of sleep in a patient.

Particularly, short acting GABAergic agonists such as zopiclone and eszopiclone provide benefits on sleep onset and sleep maintenance. However, optimal sleep maintenance effects may only be seen at doses that create a risk for next-day dysfunction, and which may raise unnecessary risks of memory and gait impairment, and of respiratory dysfunction. Therefore, an agent such as inhibitors of 5HT2A receptors that provides additional sleep maintenance effects, operating through a complementary mechanism, would be desired.

In addition, while zopiclone/eszopiclone do not have the negative effects on stage 3/4 sleep (Slow Wave Sleep; SWS) seen with benzodiazepines, they do not appear to significantly enhance SWS. These stages have been associated with the restorative activity of sleep, and hence enhancement of these stages, which are reduced in patients with sleep maintenance insomnia (at least as compared with young healthy volunteers), may provide improvement in daytime function, and possibly in addressing other disorders associated with aging and sleep deprivation (including increased adiposity, decreased lean body mass, and increased risk for diabetes mellitus) (Van Cauter et al., JAMA, 2000; 284:861-868).

The mechanism of serotonin 2A antagonism (5HT2A) may also facilitate circadian entrainment, an issue in older subjects who tend to have phase advancement and (especially in demented populations) a general disruption of rhythmicity of circadian processes.

It should also be noted that slow wave sleep (SWS) is associated with reduced risk of arousals and awakenings (Salzarulo et al., Sleep Research Online, 1999; 2:73-77). This may be particularly true in older subjects (Boselli et al., Sleep, 1998; 21:361-367). In addition, in older adult patients with insomnia, diminished SWS has been associated with cognitive impairments (Crenshaw & Edinger, Physiol. Behav., 1999; 66:485-492). A compound of formula (I) as disclosed herein has been found to increase SWS and decrease arousals and sleep stage shifts to wakefulness in patients with sleep maintenance insomnia.

Accordingly, it is an object of this invention to provide a combination, which allows combining the actions of the sleep aids and/or the long and short-acting hypnotic agents by improving the sleep quality and the respective effects of the short and long-acting hypnotic agents and/or sleep aids, without negative effect on the patient's waking-up phases.

Other objects and further scope of the applicability of the present invention will become apparent from the detailed description that follows.

SUMMARY OF THE INVENTION

Thus in accordance with this invention there is provided a combination of one or more hypnotic agents and one or more sleep aids. The combination of the invention comprises at least a short-acting hypnotic agent and/or a long-acting hypnotic agent and a sleep aid. In accordance with this aspect of the invention, the short and long-acting hypnotic agents are present in a galenic formulation adapted to an immediate or delayed release, and the sleep aid is present in the form of a galenic formulation adapted to an immediate-release.

More particularly, the present invention provides a combination of at least one short acting hypnotic agent with a compound, including enantiomers, stereoisomers, and tautomers of said compound and pharmaceutically acceptable salts, solvates or derivatives thereof, with said compound having the general structure shown in formula I:

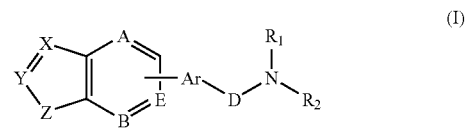

wherein:

X═Y denotes either a single or double bond between X and Y;

X is CR, CHR, CO, N, O or S;

Y is CR, CHR, CO, $S(O)_2$, N or NR;

Z is NR, CO—NR, $S(O)_2$—NR;

A, B and E are the same or different and independently from each other are CR or N;

D is either $CH_2$ or CO;

Ar is substituted or unsubstituted aryl or heteroaryl;

each R is independently chosen from hydrogen, halogen, CN, $C(O)NR_3R_4$, $C_{1-4}$alkyl, $C_{1-4}$alkoxy, $C_{1-4}$alkenyl, aryl, heteroaryl, aryl$C_{1-4}$alkyl, heteroaryl$C_{1-4}$alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1; wherein $R_3$ and $R_4$ are hydrogen or $C_{1-4}$alkyl; or $R_3$ and $R_4$ taken together with the nitrogen atom to which they are attached form an unsubstituted or at least monosubstituted heterocycle;

$R_1$ and $R_2$ are the same or different and selected independently of each other from substituted or unsubstituted aryl, heteroaryl, aryloyl, heteroaryloyl, arylsulfonyl, heteroarylsulfonyl, aryl$C_{1-4}$alkyl, heteroaryl$C_{1-4}$alkyl, amino$C_{1-4}$alkyl, $C_{1-4}$alkylamino$C_{1-4}$alkyl, $C_{3-8}$cycloalkylamino$C_{1-4}$alkyl, di$C_{3-8}$cycloalkylamino$C_{1-4}$alkyl, $C_{3-8}$cycloalkyl$C_{1-4}$alkylamino$C_{1-4}$alkyl, di$C_{1-4}$alkylaminoalkyl, heterocycle, heterocycle$C_{1-4}$alkyl, $C_{1-4}$alkylheterocycle$C_{1-4}$alkyl; or $R_1$ and $R_2$ taken together with the nitrogen atom to which they are attached form an unsubstituted or at least monosubstituted heterocycle; and wherein the substituents are selected from the group consisting of substituted or unsubstituted aryl, heteroaryl, aryl$C_{1-4}$alkyl, heteroaryl$C_{1-4}$alkyl, heterocycle, $C_{3-8}$cycloalkyl, $C_{1-4}$alkyl, $C_{1-4}$alkoxy, $C_{1-4}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $—NO_2$, $—NH_2$, $—NH(C_{1-4}alkyl)$, $—N(C_{1-4}alkyl)_2$, $—CN$, $—C(O)R_5$, $—NHC(O)(C_{1-4}alkyl)$, $—SO_2Cl$, $—SO_2(C_{1-4}alkyl)$, halogen and hydroxy; wherein $R_5$ is hydroxy, $C_{1-3}$alkoxy, —O-phenyl, —$NH_2$, —NH($C_{1-3}$ alkyl), —N($C_{1-3}$alkyl)$_2$ or phenyl;

heteroaryl is a 5 to 10-membered, aromatic, mono- or bicyclic heterocycle containing one or more heteroatoms selected from the group consisting of N, O and S;

aryl is a 6 to 10-membered, aromatic mono- or bicyclic ring; and heterocycle is a 3 to 10-membered, non-aromatic, mono- or bicyclic heterocycle containing one or more heteroatoms selected from the group consisting of N, O and S.

The combination of a short and long-acting hypnotic agents with a sleep aid allows to obtain beneficial effects on the sleep of the patient and that this effect was greater to the one when each of these two hypnotic agents and/or sleep aids are taken separately.

DETAILED DESCRIPTION OF THE INVENTION

The terms as used herein have the following meanings:

As used herein, the expression "$C_{1-6}$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-4}$alkoxy", "$C_{1-4}$thioalkyl" "$C_{1-4}$ alkoxyC$_{1-4}$alkyl", "hydroxyC$_{1-4}$alkyl", "$C_{1-4}$alkylcarbonyl", "$C_{1-4}$alkoxycarbonylC$_{1-4}$alkyl", "$C_{1-4}$alkoxycarbonyl", "aminoC$_{1-4}$alkyl", "$C_{1-4}$alkylamino", "$C_{1-4}$ alkylcarbamoylC$_{1-6}$alkyl", "$C_{1-4}$dialkylcarbamoylC$_{1-4}$ alkyl" "mono- or di-C$_{1-4}$alkylaminoC$_{1-4}$alkyl", "aminoC$_{1-4}$ alkylcarbonyl" "diphenylC$_{1-4}$alkyl", "phenylC$_{1-4}$alkyl", "phenylcarboylC$_{1-4}$ alkyl" and "phenoxyC$_{1-4}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$ alkynyl" includes ethynyl and propynyl, and straight-chained or branched butynyl, pentynyl and hexynyl groups.

As used herein the expression "$C_{1-4}$acyl" shall have the same meaning as "$C_{1-6}$alkanoyl", which can also be represented structurally as "R—CO—," where R is a $C_{1-3}$alkyl as defined herein. Additionally, "$C_{1-3}$alkylcarbonyl" shall mean same as $C_{1-4}$acyl. Specifically, "$C_{1-4}$acyl" shall mean formyl, acetyl or ethanoyl, propanoyl, n-butanoyl, etc. Derived expressions such as "$C_{1-4}$acyloxy" and "$C_{1-4}$acyloxyalkyl" are to be construed accordingly.

As used herein, the expression "$C_{1-6}$ perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "arylsulfonyl," is to be construed accordingly. Specific examples of arylsulfonyl include benzenesulfonyl, p-toluenesulfonyl, and the like.

As used herein, the expression "$C_{6-12}$arylC$_{1-4}$alkyl" means that the $C_{6-12}$aryl as defined herein is further attached to $C_{1-4}$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, benzimidazolyl, indazolyl, pyridofuranyl, pyridothienyl, and the like radicals.

Similarly, the expression "heteroarylC$_{1-4}$alkyl" means that the heteroaryl as defined herein is further attached to $C_{1-4}$alkyl as defined herein. Representative examples include furanylmethyl, thienylethyl, 2-(thiophenyl)propyl, pyrrolylmethyl, isopyrrolylethyl, pyrazolylmethyl, imidazolylmethyl, and the like.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1] hept-2-yl, and triazocanyl, and the like. Derived expression "heterocycleC$_{1-4}$alkyl" is to be construed accordingly. Specific examples of heterocycleC$_{1-4}$alkyl include without any limitation the following: N-pyrrolidinylmethyl, N-pyrrolidinylethyl, pyrrolidinyl-2-methyl, 2-pyrrolidinyl-2-ethyl, and the like. Similarly, the expression "$C_{1-4}$alkylheterocycleC$_{1-4}$ alkyl" should be construed accordingly. Representative examples include without any limitation the following: N-ethyl-pyrrolidinyl-N'-methyl, 2-ethyl-N-pyrrolidinyl-ethyl, N-ethyl-pyrrolidinyl-2-methyl, 2-pyrrolidinylethyl-2-ethyl, and the like.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

As used herein, the term "prodrug" shall have the generally accepted meaning in the art. One such definition includes a pharmacologically inactive chemical entity that when metabolized or chemically transformed by a biological system such as a mammalian system is converted into a pharmacologically active substance.

The expression "stereoisomers" is a general term used for all isomers of the individual molecules that differ only in the orientation of their atoms in space. Typically it includes mirror image isomers that are usually formed due to at least one asymmetric center (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

The term "solvate" as used herein means that an aggregate that consists of a solute ion or molecule with one or more solvent molecules. Similarly, a "hydrate" means that a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$perfluoroalkyl, phenyl, hydroxy, —$CO_2H$, an ester, an amide, $C_1$-$C_6$alkoxy, $C_1$-$C_6$thioalkyl, $C_1$-$C_6$ perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the combination or composition which is effective in treating the named disease, disorder or condition.

"Administering" comprises administration via any appropriate route such as oral, sublingual, buccal, transdermal, inhalation, rectal or injection (including intramuscular, intravenous, subcutaneous, etc.), or any other appropriate method of providing the combination or the composition to the patient.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

The term "short acting hypnotic agent" is referred to a compound and/or agent that is capable of inducing sleep, i.e., the entry time into the sleep phase.

The term "long acting hypnotic agent" is referred to a compound or agent that is mainly a sleep inducer but may also be capable of improving sleep quality and/or maintenance in a patient.

The term "sleep aid" is referred to a compound or agent that is mainly used to improve sleep quality and/or sleep maintenance in a patient, in particular the deep sleep phases.

The term "restorative sleep" means sleep which produces a rested state upon waking.

The term "sleep disorder" as used herein shall mean all of the description as delineated in the Diagnostic and Statistical Manual of Mental Disorders, $4^{th}$ Edition (1994), hereafter referred to as DSM-IV, published by the American Psychiatric Association. Specific sleep disorders that can be treated in accordance with this invention include without any limitation insomnia, primary insomnia, sleep maintenance insomnia, insomnia related to another mental disorder, substance induced insomnia and obstructive sleep apnea. Further description and discussion of sleep disorders are found in the International Classification of Sleep Disorders: Diagnostic and Coding Manual (1990), published by the American Sleep Disorders Association.

The term "insomnia" as used herein includes all sleep disorders, which are not caused due to other factors such as mental disorders, other medical conditions and substance induced sleep disorders. Insomnia as used herein shall also mean primary sleep disorders as defined in DSM-IV, which includes two sub-categories, namely, dyssomnias and parasomnias.

The term "primary insomnia" shall mean all of the definitions provided in DSM-IV. In addition, "primary insomnia" as used herein also includes "sleep maintenance insomnia." The DSM-IV lists the diagnostic criteria for primary insomnia as follows:
  A. The predominant complaint is difficulty initiating or maintaining sleep, or nonrestorative sleep, for at least one month.
  B. The sleep disturbance (or associated day time fatigue) causes clinically significant distress or impairment in social, occupational, or other important areas of functioning.
  C. The sleep disturbance does not occur exclusively during the course of narcolepsy, breathing-related sleep disorder, circadian rhythm sleep disorder, or a parasomnia.
  D. The disturbance does not occur exclusively during the course of another mental disorder (e.g., major depressive disorder, generalized anxiety disorder, a delirium).
  E. The disturbance is not due to the direct physiological effects of a substance (e.g., a drug of abuse, a medication) or a general medical condition.

The term "sleep disorder related to another mental disorder" as used herein includes both insomnia and hypersomnia related to another mental disorder. The DSM-IV lists the diagnostic criteria for insomnia related to another mental disorder as follows:
  A. The predominant complaint is difficulty initiating or maintaining sleep, or nonrestorative sleep, for at least one month that is associated with daytime fatigue or impaired daytime functioning.
  B. The sleep disturbance (or daytime sequalae) causes clinically significant distress or impairment in social, occupational, or other important areas of functioning.
  C. The insomnia is judged to be related to another axis I or axis II disorder (e.g., major depressive disorder, generalized anxiety disorder, adjustment disorder with anxiety, schizophrenia, etc.), but is sufficiently severe to warrant independent clinical attention.

D. The disturbance is not better accounted for by another sleep disorder (e.g., narcolepsy, breathing-related sleep disorder, a parasomnia).

E. The disturbance is not due to the direct physiological effects of a substance (e.g., a drug of abuse, a medication) or a general medical condition.

Similarly, the DSM-UV lists the diagnostic criteria for hypersomnia related to another mental disorder as follows:

A. The predominant complaint is excessive sleepiness for at least one month as evidenced by either prolonged sleep episodes or daytime sleep episodes that occur almost daily.

B. The excessive sleepiness causes clinically significant distress or impairment in social, occupational, or other important areas of functioning.

C. The hypersomnia is judged to be related to another axis I or axis II disorder (e.g., major depressive disorder, dysthymic disorder, schizophrenia, etc.), but is sufficiently severe to warrant independent clinical attention.

D. The disturbance is not better accounted for by another sleep disorder (e.g., narcolepsy, breathing-related sleep disorder, a parasomnia) or by an inadequate amount of sleep.

E. The disturbance is not due to the direct physiological effects of a substance (e.g., a drug of abuse, a medication) or a general medical condition.

The term "substance induced sleep disorder" as used herein means a prominent disturbance in sleep that is sufficiently severe to warrant independent clinical attention and is judged to be due to the direct physiological effects of a substance (i.e., a drug of abuse, a medication, or toxin exposure). Specific examples of drug of abuse, a medication or toxin exposure as referred to herein include without any limitations caffeine, alcohol, amphetamine, opioids, sedatives, hypnotics, anxiolytics, and the like. The DSM-IV lists the diagnostic criteria for substance induced sleep disorder as follows:

A. A prominent disturbance in sleep that is sufficiently severe to warrant independent clinical attention.

B. There is evidence from the history, physical examination, or laboratory findings of either (1) or (2): (1) the symptoms in criterion A developed during, or within a month of, substance intoxication or withdrawal; (2) medication use is etiologically related to the sleep disturbance.

C. The disturbance is not better accounted for by a sleep disorder that is not substance induced. Evidence that the symptoms are better accounted for by a sleep disorder that is not substance induced might include the following: the symptoms precede the onset of the substance use (or medication use); the symptoms persist for a substantial period of time (e.g., about a month) after the cessation of acute withdrawal or severe intoxication, or are substantially in excess of what would be expected given the type or amount of the substance used or the duration of use; or there is evidence that suggests the existence of an independent non-substance-induced sleep disorder (e.g., a history of recurrent non-substance-related episodes).

D. The disturbance does not occur exclusively during the course of a delirium.

E. The sleep disturbance causes clinically significant distress or impairment in social, occupational, or other important areas of functioning.

As used herein "withdrawal" refers to a syndrome characterized by untoward physical changes that occur following cessation of or reduction in substance use, or administration of a pharmacologic antagonist (or medication).

The term "obstructive sleep apnea" as used herein is breathing related sleep disorder as defined in DSM-IV. It is also referred to as upper airway resistance syndrome and generally involves repeated episodes of upper-airway obstruction during sleep and is normally characterized by loud snores or brief gasps that alternate with episodes of silence. The DSM-IV lists the diagnostic criteria for breathing related sleep disorder as follows:

A. Sleep disruption, leading to excessive sleepiness or insomnia, that is judged to be due to a sleep-related breathing condition (e.g., obstructive sleep or central sleep apnea syndrome or central alveolar hypoventilation syndrome).

B. The disturbance is not better accounted for by another mental disorder and is not due to the direct physiological effects of a substance (e.g., a drug of abuse, a medication) or another general medical condition (other than a breathing related disorder).

Subjective and Objective Determinations of Sleep Disorders: There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times does the patient wake up during the night, how restless is the patient during sleep, etc. Another method is to objectively measure the stages of sleep.

Polysomnography is the monitoring of multiple electrophysiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) which may be an indication of the quality of sleep.

There are five distinct sleep stages which can be measured by polysomnography: rapid eye movement (REM) sleep and four stages of no-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep) are the deepest levels of sleep and occupy about 10-20% of sleep time. REM sleep, during which the majority of typical story like dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

Thus in accordance with this invention there is provided a combination of two hypnotic agents, or at least one hypnotic agent and at least one sleep aid. The combination of the invention comprises at least a short or long-acting hypnotic agent and a sleep aid. In accordance with this aspect of the invention, the short or long-acting hypnotic agent is present in a galenic formulation adapted to an immediate or delayed release, and the sleep aid is present in the form of a galenic formulation adapted to an immediate-release.

More particularly, the present invention provides a combination of at least one short acting hypnotic agent with a compound of formula I as described hereinbelow. The compound of formula I is also described in U.S. Provisional Patent Application No. 60/651,911, which is incorporated herein by reference.

The compound including its enantiomers, stereoisomers, and tautomers and pharmaceutically acceptable salts, solvates or derivatives thereof can be used with the combination of this invention; with said compound having the general structure shown in formula I:

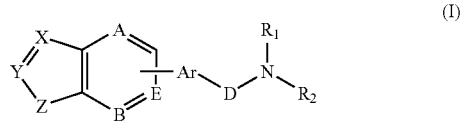

wherein:
X═Y denotes either a single or double bond between X and Y;
X is CR, CHR, CO, N, O or S;
Y is CR, CHR, CO, S(O)$_2$, N or NR;
Z is NR, CO—NR, S(O)$_2$—NR;
A, B and E are the same or different and independently from each other are CR or N;
D is either CH$_2$ or CO;
Ar is substituted or unsubstituted aryl or heteroaryl;
each R is independently chosen from hydrogen, halogen, CN, C(O)NR$_3$R$_4$, C$_{1-4}$alkyl, C$_{1-4}$alkoxy, C$_{1-4}$alkenyl, aryl, heteroaryl, arylC$_{1-4}$alkyl, heteroarylC$_{1-4}$alkyl, fluoroalkyl or fluoroalkoxy of the formula C$_n$H$_x$F$_y$ or OC$_n$H$_x$F$_y$ wherein n is an integer from 1 to 4, x is an integer from 0 to 8, y is an integer from 1 to 9 and sum of x and y is 2n+1; wherein
R$_3$ and R$_4$ are hydrogen or C$_{1-4}$alkyl; or
R$_3$ and R$_4$ taken together with the nitrogen atom to which they are attached form an unsubstituted or at least monosubstituted heterocycle;
R$_1$ and R$_2$ are the same or different and selected independently of each other from substituted or unsubstituted aryl, heteroaryl, aryloyl, heteroaryloyl, arylsulfonyl, heteroarylsulfonyl, arylC$_{1-4}$alkyl, heteroarylC$_{1-4}$alkyl, aminoC$_{1-4}$alkyl, C$_{1-4}$alkylaminoC$_{1-4}$alkyl, C$_{3-8}$cycloalkylaminoC$_{1-4}$alkyl, diC$_{3-8}$cycloalkylaminoC$_{1-4}$alkyl, C$_{3-8}$cycloalkylC$_{1-4}$alkylaminoC$_{1-4}$alkyl, diC$_{1-4}$alkylaminoalkyl, heterocycle, heterocycleC$_{1-4}$alkyl, C$_{1-4}$alkylheterocycleC$_{1-4}$alkyl; or
R$_1$ and R$_2$ taken together with the nitrogen atom to which they are attached form an unsubstituted or at least monosubstituted heterocycle; and wherein
the substituents are selected from the group consisting of substituted or unsubstituted aryl, heteroaryl, arylC$_{1-4}$alkyl, heteroarylC$_{1-4}$alkyl, heterocycle, C$_{3-8}$cycloalkyl, C$_{1-4}$alkyl, C$_{1-4}$alkoxy, C$_{1-4}$alkenyl, fluoroalkyl or fluoroalkoxy of the formula C$_n$H$_x$F$_y$ or OC$_n$H$_x$Y wherein n is an integer from 1 to 4, x is an integer from 0 to 8, y is an integer from 1 to 9 and sum of x and y is 2n+1, —NO$_2$, —NH$_2$, —NH(C$_{1-4}$alkyl), —N(C$_{1-4}$alkyl)$_2$, —CN, —C(O)R$_5$, —NHC(O)(C$_{1-4}$alkyl), —SO$_2$Cl, —SO$_2$(C$_{1-4}$alkyl), halogen and hydroxy; wherein
R$_5$ is hydroxy, C$_{1-3}$alkoxy, —O-phenyl, —NH$_2$, —NH(C$_{1-3}$ alkyl), —N(C$_{1-3}$alkyl)$_2$ or phenyl;
heteroaryl is a 5 to 10-membered, aromatic, mono- or bicyclic heterocycle containing one or more heteroatoms selected from the group consisting of N, O and S;
aryl is a 6 to 10-membered, aromatic mono- or bicyclic ring; and
heterocycle is a 3 to 10-membered, non-aromatic, mono- or bicyclic heterocycle containing one or more heteroatoms selected from the group consisting of N, O and S.

In one aspect of this invention, the compounds of formula (I) having the following substituents are preferred:
D is CH$_2$;
Ar is substituted or unsubstituted phenyl, pyridinyl, pyrazinyl, furanyl or thiophenyl; wherein the substituents are selected from the group consisting of fluorine, chlorine, C$_{1-4}$alkyl, C$_{1-4}$alkoxy and —CF$_3$;
each R is independently chosen from hydrogen, CN or C$_{1-4}$alkyl;
R$_1$ and R$_2$ are the same or different and selected independently of each other from substituted or unsubstituted benzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, phenylC$_{0-4}$alkyl, thiophenylC$_{1-4}$alkyl, aza-bicyclo[2.2.2]octylC$_{0-4}$alkyl, aza-bicyclo[3.2.1]octylC$_{0-4}$alkyl, piperidinylC$_{0-4}$alkyl, pyrrolidinylC$_{0-4}$alkyl, C$_{1-4}$alkylaminoC$_{1-4}$alkyl and diC$_{1-4}$alkylaminoC$_{1-4}$alkyl; wherein the substituted moieties may be substituted with one or more substituents selected from the group consisting of fluorine, chlorine, C$_{1-4}$alkyl, C$_{3-8}$cycloalkyl, C$_{1-4}$alkoxy, OCF$_3$ and CF$_3$; or
R$_1$ and R$_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and C$_{1-4}$alkyl.

In a further aspect of this invention, the compounds of formula (I) with the following substituents are preferred:
X═Y denotes a double bond between X and Y;
X is CR;
Y is CR;
Z is NR;
A, B and E are the same or different and independently from each other are CH or N;
Ar is phenyl, fluorophenyl, chlorophenyl, pyridinyl, pyrazinyl, furanyl or thiophenyl;
each R is independently chosen from hydrogen, CN, methyl, ethyl, methoxy, fluorine, CF$_3$ or OCF$_3$;
R$_1$ and R$_2$ are the same or different and selected independently of each other from benzyl, fluorobenzyl, fluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, aza-bicyclo[2.2.2]octyl, aza-bicyclo[2.2.2]octylmethyl, N-methyl-piperidinyl, pyrrolidinylmethyl, pyrrolidinylethyl, pyrrolidinylpropyl and dimethylamino ethyl; or $R_1$ and $R_2$ taken together with the nitrogen atom to which they are attached form a unsubstituted or at least mono-substituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds encompassed within the above noted embodiment without any limitations include the following:

N-benzyl-N-[3-(1H-indol-5-yl)-benzyl]-N',N'-dimethyl-ethane-1,2-diamine;
4-fluoro-N-[2-fluoro-5-(1H-indol-5-yl)-benzyl]-N-(2-pyrrolidin-1-yl-ethyl)-benzamide;
N-(2-dimethylamino-ethyl)-4-fluoro-N-[2-fluoro-5-(2-methyl-1H-indol-5-yl)-benzyl]-benzamide;
N-(2-dimethylamino-ethyl)-4-fluoro-N-[2-fluoro-5-(1H-indol-5-yl)-benzyl]-benzamide;
4-fluoro-N-[3-(1H-indol-5-yl)-benzyl]-N-(1-methyl-piperidin-4-yl)-benzamide;
thiophene-2-carboxylic acid [3-(1H-indol-5-yl)-benzyl]-(1-methyl-piperidin-4-yl)-amide;
thiophene-2-carboxylic acid [2-fluoro-5-(1H-indol-5-yl)-benzyl]-(1-methyl-piperidin-4-yl)-amide;
thiophene-2-carboxylic acid (2-dimethylamino-ethyl)-[2-fluoro-5-(1H-indol-5-yl)-benzyl]-amide;
4-fluoro-N-[2-fluoro-5-(1H-indol-5-yl)-benzyl]-N-(1-methyl-piperidin-4-yl)-benzamide;
N-(1-aza-bicyclo[2.2.2]oct-4-ylmethyl)-4-fluoro-N-[2-fluoro-5-(1H-indol-5-yl)-benzyl]-benzamide trifluoro-acetate;
4-fluoro-N-[5-(1H-indol-5-yl)-pyridin-3-ylmethyl]-N-(2-pyrrolidin-1-yl-ethyl)-benzamide;
4-fluoro-N-[4-fluoro-3-(1H-indol-5-yl)-benzyl]-N-(1-methyl-piperidin-4-yl)-benzamide;
4-fluoro-N-[4-(1H-indol-5-yl)-thiophen-2-ylmethyl]-N-(2-pyrrolidin-1-yl-ethyl)-benzamide acetate;
(4-fluoro-benzyl)-[2-fluoro-5-(1H-indol-5-yl)-benzyl]-(1-methyl-piperidin-4-yl)-amine;
N-(4-fluoro-benzyl)-N-[2-fluoro-5-(1H-indol-5-yl)-benzyl]-N',N'-dimethyl-ethane-1,2-diamine;
(1-aza-bicyclo[2.2.2]oct-4-ylmethyl)-(4-fluoro-benzyl)-[2-fluoro-5-(1H-indol-5-yl)-benzyl]-amine acetate;
N-(2-dimethylamino-ethyl)-4-fluoro-N-[5-(1H-indol-5-yl)-pyridin-3-ylmethyl]-benzamide trifluoroacetate;
4-fluoro-N-[5-(1H-indol-5-yl)-thiophen-2-ylmethyl]-N-(2-pyrrolidin-1-yl-ethyl)-benzamide;
4-fluoro-N-[4-(1H-indol-5-yl)-furan-2-ylmethyl]-N-(1-methyl-piperidin-4-yl)-benzamide;
N-(1-aza-bicyclo[2.2.2]oct-3R-yl)-4-fluoro-N-[2-fluoro-5-(1H-indol-6-yl)-benzyl]-benzamide;
pyrimidine-4-carboxylic acid [2-fluoro-5-(1H-indol-5-yl)-benzyl]-(1-methyl-piperidin-4-yl)-amide;
pyrimidine-2-carboxylic acid [2-fluoro-5-(1H-indol-5-yl)-benzyl]-(1-methyl-piperidin-4-yl)-amide;
pyridazine-3-carboxylic acid [2-fluoro-5-(1H-indol-5-yl)-benzyl]-(1-methyl-piperidin-4-yl)-amide;
pyridazine-4-carboxylic acid [2-fluoro-5-(1H-indol-5-yl)-benzyl]-(1-methyl-piperidin-4-yl)-amide;
2,3-dihydro-benzo[1,4]dioxine-6-carboxylic acid [2-fluoro-5-(1H-indol-5-yl)-benzyl]-(1-methyl-piperidin-4-yl)-amide;
N-[2-fluoro-5-(1H-indol-5-yl)-benzyl]-4-isopropoxy-N-(1-methyl-piperidin-4-yl)-benzamide;
N-[2-fluoro-5-(1H-indol-5-yl)-benzyl]-3-isopropoxy-N-(1-methyl-piperidin-4-yl)-benzamide;
N-[2-fluoro-5-(1H-indol-5-yl)-benzyl]-N-(1-methyl-piperidin-4-yl)-4-trifluoromethoxy-benzamide;
4-chloro-N-[2-fluoro-5-(1H-indol-5-yl)-benzyl]-N-(1-methyl-piperidin-4-yl)-benzamide;
benzo[1,3]dioxole-5-carboxylic acid [2-fluoro-5-(1H-indol-5-yl)-benzyl]-(1-methyl-piperidin-4-yl)-amide;
N-[2-fluoro-5-(1H-indol-5-yl)-benzyl]-N-(1-methyl-piperidin-4-yl)-4-trifluoromethyl-benzamide;
4-fluoro-N-[2-fluoro-5-(1H-indol-5-yl)-benzyl]-N-(1-methyl-piperidin-4-yl)-3-trifluoromethyl-benzamide;
N-[2-fluoro-5-(1H-indol-5-yl)-benzyl]-N-(1-methyl-piperidin-4-yl)-isonicotinamide;
N-[3-(1H-indol-5-yl)-benzyl]-N-(1-methyl-piperidin-4-yl)-4-trifluoromethyl-benzamide;
4-fluoro-N-[4-fluoro-3-(1H-indol-5-yl)-benzyl]-N-(2-pyrrolidin-1-yl-ethyl)-benzamide;
N-[2-fluoro-5-(1H-indol-5-yl)-benzyl]-N-(2-pyrrolidin-1-yl-ethyl)-4-trifluoromethyl-benzamide;
4-fluoro-N-[3-fluoro-5-(1H-indol-5-yl)-benzyl]-N-(2-pyrrolidin-1-yl-ethyl)-benzamide;
N-[3-(1H-indol-5-yl)-benzyl]-N-(2-pyrrolidin-1-yl-ethyl)-4-trifluoromethyl-benzamide;
N-[3-(1H-indol-5-yl)-benzyl]-N-(2-pyrrolidin-1-yl-ethyl)-isonicotinamide;
N-[4-fluoro-3-(1H-indol-5-yl)-benzyl]-N-(2-pyrrolidin-1-yl-ethyl)-4-trifluoromethyl-benzamide;
N-[3-(1H-indol-5-yl)-benzyl]-N-(3-pyrrolidin-1-yl-propyl)-isonicotinamide;
N-[4-fluoro-3-(1H-indol-5-yl)-benzyl]-N-(3-pyrrolidin-1-yl-propyl)-isonicotinamide;
pyridine-2-carboxylic acid [3-(1H-indol-5-yl)-benzyl]-(3-pyrrolidin-1-yl-propyl)-amide;
N-[3-(1H-indol-5-yl)-benzyl]-N-(3-pyrrolidin-1-yl-propyl)-4-trifluoromethyl-benzamide;
pyridine-2-carboxylic acid [4-fluoro-3-(1H-indol-5-yl)-benzyl]-(3-pyrrolidin-1-yl-propyl)-amide;
pyridine-2-carboxylic acid [4-(1H-indol-5-yl)-thiophen-2-ylmethyl]-(3-pyrrolidin-1-yl-propyl)-amide;
N-[4-(1H-indol-5-yl)-thiophen-2-ylmethyl]-N-(3-pyrrolidin-1-yl-propyl)-4-trifluoromethyl-benzamide;
N-[4-(1H-indol-5-yl)-thiophen-2-ylmethyl]-N-(2-pyrrolidin-1-yl-ethyl)-isonicotinamide;
pyridine-2-carboxylic acid [4-(1H-indol-5-yl)-thiophen-2-ylmethyl]-(2-pyrrolidin-1-yl-ethyl)-amide;
N-[4-(1H-indol-5-yl)-thiophen-2-ylmethyl]-N-(2-pyrrolidin-1-yl-ethyl)-4-trifluoromethyl-benzamide;
pyridine-2-carboxylic acid [4-(1H-indol-5-yl)-furan-2-ylmethyl]-(3-pyrrolidin-1-yl-propyl)-amide;
N-[4-(1H-indol-5-yl)-furan-2-ylmethyl]-N-(3-pyrrolidin-1-yl-propyl)-4-trifluoromethyl-benzamide;
N-[4-(1H-indol-5-yl)-furan-2-ylmethyl]-N-(2-pyrrolidin-1-yl-ethyl)-isonicotinamide;
pyridine-2-carboxylic acid [4-(1H-indol-5-yl)-furan-2-ylmethyl]-(2-pyrrolidin-1-yl-ethyl)-amide;
N-[4-(1H-indol-5-yl)-furan-2-ylmethyl]-N-(2-pyrrolidin-1-yl-ethyl)-4-trifluoromethyl-benzamide;
N-[4-(1H-indol-5-yl)-thiophen-2-ylmethyl]-N-(3-pyrrolidin-1-yl-propyl)-isonicotinamide;
N-[4-(1H-indol-5-yl)-furan-2-ylmethyl]-N-(3-pyrrolidin-1-yl-propyl)-isonicotinamide;
N-[2-chloro-5-(1H-indol-5-yl)-benzyl]-N-(1-methyl-piperidin-4-yl)-isonicotinamide;

pyridine-2-carboxylic acid [2-fluoro-5-(1H-indol-5-yl)-benzyl]-(1-methyl-piperidin-4-yl)-amide;
N-[2-fluoro-5-(1H-indol-5-yl)-benzyl]-N-(1-methyl-piperidin-4-yl)-nicotinamide;
N-[2-fluoro-5-(1H-indol-5-yl)-benzyl]-N-(1-methyl-piperidin-4-yl)-3-trifluoromethoxy-benzamide;
N-[2-fluoro-5-(1H-indol-5-yl)-benzyl]-N-(2-pyrrolidin-1-yl-ethyl)-isonicotinamide;
N-[4-fluoro-3-(1H-indol-5-yl)-benzyl]-N-(2-pyrrolidin-1-yl-ethyl)-isonicotinamide;
N-[4-fluoro-3-(1H-indol-5-yl)-benzyl]-N-(2-pyrrolidin-1-yl-ethyl)-4-trifluoromethoxy-benzamide acetate;
N-[3-(1H-indol-5-yl)-benzyl]-N-(1-methyl-piperidin-4-yl)-isonicotinamide;
pyrazine-2-carboxylic acid [2-fluoro-5-(1H-indol-5-yl)-benzyl]-(1-methyl-piperidin-4-yl)-amide;
5-[4-fluoro-3-(4-methyl-2-pyridin-3-yl-piperazin-1-ylmethyl)-phenyl]-1H-indole acetate;
5-{4-fluoro-3-[4-methyl-2-(4-trifluoromethyl-phenyl)-piperazin-1-ylmethyl]-phenyl}-1H-indole;
5-[4-fluoro-3-(4-methyl-2-pyridin-2-yl-piperazin-1-ylmethyl)-phenyl]-1H-indole acetate;
5-{5-[2S-(4-fluoro-phenyl)-4-methyl-piperazin-1-ylmethyl]-pyridin-3-yl}-1H-indole acetate;
5-{4-fluoro-3-[2S-(4-fluoro-phenyl)-4-methyl-piperazin-1-ylmethyl]-phenyl}-1H-indole;
5-[4-fluoro-3-(2-furan-2-yl-4-methyl-piperazin-1-ylmethyl)-phenyl]-1H-indole;
5-{5-[2S-(4-fluoro-phenyl)-4-methyl-piperazin-1-ylmethyl]-furan-3-yl}-1H-indole trifluoro-acetate;
5-{5-[2S-(4-fluoro-phenyl)-piperazin-1-ylmethyl]-pyridin-3-yl}-1H-indole acetate;
5-{5-[2S-(4-fluoro-phenyl)-piperazin-1-ylmethyl]-furan-3-yl}-1H-indole;
5-[3-(4-methyl-piperazin-1-ylmethyl)-phenyl]-1H-indole;
5-[4-fluoro-3-(4-methyl-2-pyridin-4-yl-piperazin-1-ylmethyl)-phenyl]-1H-indole;
5-{3-[2S-(4-fluoro-phenyl)-4-methyl-piperazin-1-ylmethyl]-phenyl}-1H-indole;
5-{6-[2S-(4-fluoro-phenyl)-4-methyl-piperazin-1-ylmethyl]-pyrazin-2-yl}-1H-indole acetate;
5-{4-fluoro-3-[2S-(4-fluoro-phenyl)-piperazin-1-ylmethyl]-phenyl}-1H-indole acetate;
5-{4-fluoro-3-[2S-(4-fluoro-phenyl)-4-methyl-piperazin-1-ylmethyl]-phenyl}-1H-indole-3-carbonitrile;
5-[3-(4-methyl-[1,4]diazepan-1-ylmethyl)-phenyl]-1H-indole;
5-{4-fluoro-3-[2S-(4-fluoro-phenyl)-4-methyl-piperazin-1-ylmethyl]-phenyl}-3-methyl-1H-indole;
N-[5-(3-cyano-1H-indol-5-yl)-2-fluoro-benzyl]-N-(2-dimethylamino-ethyl)-4-fluoro-benzamide;
5-{4-fluoro-3-[2S-(4-fluoro-phenyl)-piperazin-1-ylmethyl]-phenyl}-1H-indole-3-carbonitrile;
5-(3-{[(2-dimethylamino-ethyl)-(4-fluoro-benzyl)-amino]-methyl}-4-fluoro-phenyl)-1H-indole-3-carbonitrile trifluoro-acetate;
4-fluoro-N-[2-fluoro-5-(1H-pyrrolo[3,2-b]pyridin-5-yl)-benzyl]-N-(2-pyrrolidin-1-yl-ethyl)-benzamide;
5-{4-fluoro-3-[2-(4-fluoro-phenyl)-4-methyl-piperazin-1-ylmethyl]-phenyl}-1H-pyrrolo[3,2-b]pyridine; and
4-fluoro-N-[2-fluoro-5-(1H-pyrrolo[2,3-c]pyridin-5-yl)-benzyl]-N-(2-pyrrolidin-1-yl-ethyl)-benzamide;
 or a pharmaceutically acceptable salt thereof or an optical or stereoisomer thereof.

In yet another embodiment of this invention, the compounds of formula (I) having the following substituents are also preferred:

X=Y denotes a double bond between X and Y;
X is CR;
Y is N;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl, ethyl, methoxy, fluorine, $CF_3$ or $OCF_3$;
$R_1$ and $R_2$ are the same or different and selected independently of each other from benzyl, fluorobenzyl, fluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, N-methyl-aza-bicyclo[2.2.2]octyl, aza-bicyclo[2.2.2]octyl, aza-bicyclo[2.2.2]octylmethyl, N-methyl-piperidinyl, piperidinyl, N-methyl-pyrrolidinyl, pyrrolidinylmethyl, pyrrolidinylethyl, pyrrolidinylpropyl, methylaminoethyl, and dimethylaminoethyl;
or
$R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds within the scope of this embodiment without any limitations may be enumerated as follows:
N-benzyl-N-[3-(H-indazol-5-yl)-benzyl]-N',N'-dimethyl-ethane-1,2-diamine hydrochloride;
N-(4-fluoro-benzyl)-N-[5-(1H-indazol-5-yl)-pyridin-3-ylmethyl]-N',N'-dimethyl-ethane-1,2-diamine acetate;
(4-fluoro-benzyl)-[2-fluoro-5-(1H-indazol-5-yl)-benzyl]-pyrrolidin-2S-ylmethyl-amine;
(4-fluoro-benzyl)-[2-fluoro-5-(1H-indazol-5-yl)-benzyl]-piperidin-4-yl-amine;
N-(4-fluoro-benzyl)-N-[2-fluoro-5-(1H-indazol-5-yl)-benzyl]-N'-methyl-ethane-1,2-diamine;
(4-fluoro-benzyl)-[2-fluoro-5-(1H-indazol-5-yl)-benzyl]-(1-methyl-piperidin-4-yl)-amine;
(4-fluoro-benzyl)-[4-(1H-indazol-5-yl)-furan-2-ylmethyl]-(1-methyl-piperidin-4-yl)-amine;
4-fluoro-N-[2-fluoro-5-(1H-indazol-5-yl)-benzyl]-N-(2-pyrrolidin-1-yl-ethyl)-benzamide;
4-fluoro-N-[2-fluoro-5-(1H-indazol-5-yl)-benzyl]-N-(exo-8-methyl-8-aza-bicyclo[3.2.1]oct-3-yl)-benzamide;
4-fluoro-N-[2-fluoro-5-(1H-indazol-5-yl)-benzyl]-N-(endo-8-methyl-8-aza-bicyclo[3.2.1]oct-3-yl)-benzamide;
4-fluoro-N-[2-fluoro-5-(1H-indazol-5-yl)-benzyl]-N-(1-methyl-piperidin-3-yl)-benzamide;
4-fluoro-N-[2-fluoro-5-(1H-indazol-5-yl)-benzyl]-N-(1-methyl-piperidin-3S-yl)-benzamide trifluoro-acetate;
4-fluoro-N-[2-fluoro-5-(1H-indazol-5-yl)-benzyl]-N-(1-methyl-pyrrolidin-3R-yl)-benzamide trifluoro-acetate;
4-fluoro-N-[2-fluoro-5-(1H-indazol-5-yl)-benzyl]-N-(1-methyl-pyrrolidin-3S-yl)-benzamide trifluoro-acetate;
4-fluoro-N-[2-fluoro-5-(1H-indazol-5-yl)-benzyl]-N-(3-pyrrolidin-1-yl-propyl)-benzamide;
4-fluoro-N-[2-fluoro-5-(1H-indazol-5-yl)-benzyl]-N-(1-methyl-piperidin-4-yl)-benzamide;
N-(1-aza-bicyclo[2.2.2]oct-3R-yl)-4-fluoro-N-[2-fluoro-5-(1H-indazol-5-yl)-benzyl]-benzamide;

chiral N-[2-fluoro-5-(1H-indazol-5-yl)-benzyl]-N-(1-methyl-pyrrolidin-3R-yl)-4-trifluoromethyl-benzamide;
4-fluoro-N-[4-(1H-indazol-5-yl)-furan-2-ylmethyl]-N-(1-methyl-piperidin-4-yl)-benzamide;
5-{4-fluoro-3-[2-(4-fluoro-phenyl)-piperazin-1-ylmethyl]-phenyl}-1H-indazole;
5-[4-fluoro-3-(2S-thiophen-2-yl-piperazin-1-ylmethyl)-phenyl]-1H-indazole acetate;
5-[4-fluoro-3-(2-thiophen-2-yl-piperazin-1-ylmethyl)-phenyl]-1H-indazole;
chiral 5-[4-fluoro-3-(2-thiophen-2-yl-piperazin-1-ylmethyl)-phenyl]-1H-indazole acetate;
5-{4-fluoro-3-[2S-(4-fluoro-phenyl)-4-methyl-piperazin-1-ylmethyl]-phenyl}-1H-indazole;
5-{5-[2S-(4-fluoro-phenyl)-4-methyl-piperazin-1-ylmethyl]-pyridin-3-yl}-1H-indazole;
5-{5-[2S-(4-fluoro-phenyl)-piperazin-1-ylmethyl]-pyridin-3-yl}-1H-indazole;
5-{5-[2S-(4-fluoro-phenyl)-piperazin-1-ylmethyl]-furan-3-yl}-1H-indazole;
5-[4-fluoro-3-(4-methyl-2R-thiophen-2-yl-piperazin-1-ylmethyl)-phenyl]-1H-indazole acetate;
5-[4-fluoro-3-(4-methyl-2S-thiophen-2-yl-piperazin-1-ylmethyl)-phenyl]-1H-indazole acetate; and
5-{5-[2S-(4-fluoro-phenyl)-4-methyl-piperazin-1-ylmethyl]-furan-3-yl}-1H-indazole;
or a pharmaceutically acceptable salt thereof or an optical or stereoisomer thereof.

In another embodiment, compounds of formula (I) having the following substituents are preferred:
X=Y denotes a double bond between X and Y;
X is N;
Y is CR;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl, ethyl, methoxy, $CF_3$ or $OCF_3$;
$R_1$ and $R_2$ are the same or different and selected independently of each other from benzyl, fluorobenzyl, fluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, N-methyl-aza-bicyclo[2.2.2]octyl, aza-bicyclo[2.2.2]octyl, aza-bicyclo[2.2.2]octylmethyl, N-methyl-piperidinyl, piperidinyl, N-methyl-pyrrolidinyl, pyrrolidinylmethyl, pyrrolidinylethyl, pyrrolidinylpropyl, methylaminoethyl, dimethylaminoethyl and dimethylaminopropyl;
or
$R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Specific examples of compounds within the scope of this embodiment without any limitations are listed as follows:
N-[3-(1H-benzoimidazol-5-yl)-benzyl]-N-benzyl-N',N'-dimethyl-ethane-1,2-diamine hydrochloride; and
N-[3-(1H-benzoimidazol-5-yl)-benzyl]-N-benzyl-N',N'-dimethyl-propane-1,3-diamine hydrochloride;
or a pharmaceutically acceptable salt thereof or an optical or stereoisomer thereof.

In another embodiment of this invention the compound of formula (I) is having the following substituents:
X=Y denotes a double bond between X and Y;
X is N;
Y is N;
Z is NR;
A, B and E are CH;
Ar is phenyl, fluorophenyl, chlorophenyl, pyridinyl, pyrazinyl, furanyl or thiophenyl;
R is hydrogen, methyl or ethyl;
$R_1$ and $R_2$ are the same or different and selected independently of each other from benzyl, fluorobenzyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;
or
$R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds of formula (I) falling within the scope of the above noted embodiment include without any limitations the following:
N-[3-(1H-benzotriazol-5-yl)-benzyl]-N-benzyl-N',N'-dimethyl-propane-1,3-diamine;
[5-(1H-benzotriazol-5-yl)-2-fluoro-benzyl]-(4-fluoro-benzyl)-pyrrolidin-2R-ylmethyl-amine trihydrochloride;
[5-(1H-benzotriazol-5-yl)-2-fluoro-benzyl]-piperidin-4-yl-thiophen-2-ylmethyl-amine;
[5-(1H-benzotriazol-5-yl)-2-fluoro-benzyl]-(4-fluoro-benzyl)-piperidin-4-yl-amine;
N-[5-(1H-benzotriazol-5-yl)-2-fluoro-benzyl]-N-(4-fluoro-benzyl)-N'-methyl-ethane-1,2-diamine;
[5-(1H-benzotriazol-5-yl)-2-fluoro-benzyl]-(1-ethyl-pyrrolidin-2S-ylmethyl)-(4-fluoro-benzyl)-amine hydrochloride;
[5-(1H-benzotriazol-5-yl)-2-fluoro-benzyl]-(4-fluoro-benzyl)-(1-methyl-piperidin-4-yl)-amine hydrochloride;
N-[3-(1H-benzotriazol-5-yl)-benzyl]-N-benzyl-N',N'-dimethyl-ethane-1,2-diamine hydrochloride;
N-[5-(1H-benzotriazol-5-yl)-2-fluoro-benzyl]-N-(1-ethyl-pyrrolidin-2S-ylmethyl)-4-fluoro-benzamide;
N-[3-(1H-benzotriazol-5-yl)-benzyl]-4-fluoro-N-(2-pyrrolidin-1-yl-ethyl)-benzamide hydrochloride;
thiophene-2-carboxylic acid [5-(1H-benzotriazol-5-yl)-2-fluoro-benzyl]-(2-pyrrolidin-1-yl-ethyl)-amide hydrochloride;
N-[5-(1H-benzotriazol-5-yl)-2-fluoro-benzyl]-2,4-difluoro-N-(2-pyrrolidin-1-yl-ethyl)-benzamide hydrochloride;
N-[5-(1H-benzotriazol-5-yl)-2-fluoro-benzyl]-4-fluoro-N-(2-pyrrolidin-1-yl-ethyl)-benzamide;

N-[5-(1H-benzotriazol-5-yl)-2-fluoro-benzyl]-4-fluoro-N-piperidin-4-yl-benzamide;

N-[5-(1H-benzotriazol-5-yl)-2-fluoro-benzyl]-4-fluoro-N-(1-isopropyl-piperidin-4-yl)-benzamide;

N-[5-(1H-benzotriazol-5-yl)-2-fluoro-benzyl]-N-(1-cyclopropyl-piperidin-4-yl)-4-fluoro-benzamide;

N-[5-(1H-benzotriazol-5-yl)-2-fluoro-benzyl]-N-(1-methyl-piperidin-4-yl)-4-fluoro-benzamide;

5-[3-(4-methyl-piperazin-1-ylmethyl)-phenyl]-1H-benzotriazole;

5-[4-fluoro-3-(4-methyl-piperazin-1-ylmethyl)-phenyl]-1H-benzotriazole; and

5-{4-fluoro-3-[2S-(4-fluoro-phenyl)-piperazin-1-ylmethyl]-phenyl}-1H-benzotriazole;

or a pharmaceutically acceptable salt thereof or an optical or stereoisomer thereof.

In yet another embodiment of this invention the compound of formula (I) is having the following substituents:

X═Y denotes a single bond between X and Y;
X is CHR;
Y is CHR;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl, ethyl or $CF_3$;
$R_1$ and $R_2$ are the same or different and selected independently of each other from benzyl, fluorobenzyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;

or $R_1$ and $R_2$ taken together with the nitrogen atom to which they are attached form a unsubstituted or at least mono-substituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

An example of a compound of formula (I) falling within the scope of the above noted embodiment includes without any limitations the following:

N-[5-(2,3-dihydro-1H-indol-5-yl)-2-fluoro-benzyl]-N-(2-dimethylamino-ethyl)-4-fluoro-benzamide;

or a pharmaceutically acceptable salt thereof or an optical or stereoisomer thereof.

In yet another embodiment of this invention the compound of formula (I) is having the following substituents:

X═Y denotes a single bond between X and Y;
X is O, S or NR;
Y is CO;
Z is NR;
A, B and E are CH;
Ar is phenyl, fluorophenyl, chlorophenyl, pyridinyl, pyrazinyl, furanyl or thiophenyl;
each R is independently chosen from hydrogen, methyl or ethyl;
$R_1$ and $R_2$ are the same or different and selected independently of each other from benzyl, fluorobenzyl, benzoyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydro-benzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;

or $R_1$ and $R_2$ taken together with the nitrogen atom to which they are attached form a unsubstituted or at least mono-substituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds of formula (I) falling within the scope of the above noted embodiment include without any limitations the following:

6-(3-{[benzyl-(2-dimethylamino-ethyl)-amino]-methyl}-phenyl)-3H-benzothiazol-2-one hydrochloride;

N-(2-dimethylamino-ethyl)-N-[3-(2-oxo-2,3-dihydro-benzothiazol-6-yl)-benzyl]-benzamide hydrochloride;

4-chloro-N-(2-dimethylamino-ethyl)-N-[3-(2-oxo-2,3-dihydro-benzothiazol-6-yl)-benzyl]-benzamide hydrochloride;

N-(3-dimethylamino-propyl)-N-[3-(2-oxo-2,3-dihydro-benzothiazol-6-yl)-benzyl]-benzamide; hydrochloride;

6-(3-{[benzyl-(2-dimethylamino-ethyl)-amino]-methyl}-phenyl)-3H-benzooxazol-2-one hydrochloride;

6-(5-{[(2-dimethylamino-ethyl)-(4-fluoro-benzyl)-amino]-methyl}-pyridin-3-yl)-3H-benzooxazol-2-one;

6-(5-{[(2-dimethylamino-ethyl)-(4-fluoro-benzyl)-amino]-methyl}-furan-3-yl)-3H-benzooxazol-2-one;

6-(3-{[(1-ethyl-pyrrolidin-2R-ylmethyl)-(4-fluoro-benzyl)-amino]-methyl}-4-fluoro-phenyl)-3H-benzooxazol-2-one trifluoro-acetate;

6-(4-fluoro-3-{[(4-fluoro-benzyl)-(1-methyl-piperidin-4-yl)-amino]-methyl}-phenyl)-3H-benzooxazol-2-one;

6-(5-{[(4-fluoro-benzyl)-(1-methyl-piperidin-4-yl)-amino]-methyl}-furan-3-yl)-3H-benzooxazol-2-one;

4-fluoro-N-[2-fluoro-5-(2-oxo-2,3-dihydro-benzooxazol-6-yl)-benzyl]-N-(2-pyrrolidin-1-yl-ethyl)-benzamide;

N-(2-dimethylamino-ethyl)-N-[3-(2-oxo-2,3-dihydro-benzooxazol-6-yl)-benzyl]-benzamide hydrochloride;

N-(1-ethyl-pyrrolidin-2-ylmethyl)-4-fluoro-N-[2-fluoro-5-(2-oxo-2,3-dihydro-benzooxazol-6-yl)-benzyl]-benzamide;

4-chloro-N-(2-dimethylamino-ethyl)-N-[3-(2-oxo-2,3-dihydro-benzooxazol-6-yl)-benzyl]-benzamide hydrochloride;

N-(1-ethyl-pyrrolidin-2R-ylmethyl)-4-fluoro-N-[2-fluoro-5-(2-oxo-2,3-dihydro-benzooxazol-6-yl)-benzyl]-benzamide trifluoro-acetate;

4-fluoro-N-[2-fluoro-5-(2-oxo-2,3-dihydro-benzooxazol-6-yl)-benzyl]-N-(1-methyl-piperidin-4-yl)-benzamide;

N-(1-aza-bicyclo[2.2.2]oct-3S-yl)-4-fluoro-N-[2-fluoro-5-(2-oxo-2,3-dihydro-benzooxazol-6-yl)-benzyl]-benzamide hydrochloride;

N-(1-aza-bicyclo[2.2.2]oct-3R-yl)-4-fluoro-N-[2-fluoro-5-(2-oxo-2,3-dihydro-benzooxazol-6-yl)-benzyl]-benzamide hydrochloride;

N-(2-dimethylamino-ethyl)-4-fluoro-N-[2-fluoro-5-(2-oxo-2,3-dihydro-benzooxazol-6-yl)-benzyl]-benzamide;

6-[3-(4-methyl-piperazin-1-ylmethyl)-phenyl]-3H-benzooxazol-2-one;

6-{5-[2R-(4-fluoro-phenyl)-4-methyl-piperazin-1-ylmethyl]-furan-3-yl}-3H-benzooxazol-2-one;

6-{5-[2S-(4-fluoro-phenyl)-4-methyl-piperazin-1-ylmethyl]-furan-2-yl}-3H-benzooxazol-2-one;

6-{5-[2S-(4-fluoro-phenyl)-4-methyl-piperazin-1-ylmethyl]-thiophen-3-yl}-3H-benzooxazol-2-one;

6-[4-fluoro-3-(2-thiophen-2-yl-piperazin-1-ylmethyl)-phenyl]-3H-benzooxazol-2-one;

6-{5-[2S-(4-fluorophenyl)-4-methylpiperazine-1-ylmethyl]-furan-3-yl}-3H-benzoxazol-2-one;

6-{5-[2S-(4-fluoro-phenyl)-piperazin-1-ylmethyl]-furan-3-yl}-3H-benzooxazol-2-one acetate;

6-{4-fluoro-3-[2S-(4-fluoro-phenyl)-4-methyl-piperazin-1-ylmethyl]-phenyl}-3H-benzooxazol-2-one;

6-{5-[2S-(4-fluoro-phenyl)-4-methyl-piperazin-1-ylmethyl]-pyridin-3-yl}-3H-benzooxazol-2-one acetate; and 5-(3-{[benzyl-(2-dimethylamino-ethyl)-amino]-methyl}-phenyl)-1,3-dihydro-benzoimidazol-2-one hydrochloride;

or a pharmaceutically acceptable salt thereof or an optical or stereoisomer thereof.

In yet another embodiment of this invention the compound of formula (I) is having the following substituents:

X=Y denotes a single bond between X and Y;

X is O or CO;

Y is CHR or NR;

Z is CONR;

A, B and E are the same or different and independently from each other are CH or N;

Ar is phenyl, fluorophenyl, chlorophenyl, pyridinyl, pyrazinyl, furanyl or thiophenyl;

each R is independently chosen from hydrogen, methyl or ethyl;

$R_1$ and $R_2$ are the same or different and selected independently of each other from benzyl, fluorobenzyl, benzoyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydrobenzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;

or $R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

Examples of compounds of formula (I) falling within the scope of the above noted embodiment include without any limitations the following:

6-(3-{[benzyl-(2-dimethylamino-ethyl)-amino]-methyl}-phenyl)-3-methyl-1H-quinazoline-2,4-dione hydrochloride; and 7-(3-{[benzyl-(2-dimethylamino-ethyl)-amino]-methyl}-phenyl)-4H-pyrido[3,2-b][1,4]oxazin-3-one hydrochloride;

or a pharmaceutically acceptable salt thereof or an optical or stereoisomer thereof.

In yet another embodiment of this invention the compound of formula (I) is having the following substituents:

X=Y denotes a double bond between X and Y;

X is CR;

Y is CR;

Z is NR;

A, B and E are the same or different and independently from each other are CH or N;

D is CO;

Ar is phenyl, fluorophenyl, chlorophenyl, pyridinyl, pyrazinyl, furanyl or thiophenyl;

each R is independently chosen from hydrogen, methyl, ethyl, methoxy, fluorine, $CF_3$ or $OCF_3$;

$R_1$ and $R_2$ are the same or different and selected independently of each other from benzyl, fluorobenzyl, benzoyl, fluorobenzoyl, difluorobenzoyl, chlorobenzoyl, isopropoxybenzoyl, trifluoromethylbenzoyl, fluoro-trifluoromethylbenzoyl, trifluoromethoxybenzoyl, thiophenylcarbonyl, pyridinylcarbonyl, pyrazinylcarbonyl, pyrimidinylcarbonyl, pyridazinylcarbonyl, dihydrobenzo[1,4]dioxinylcarbonyl, benzo[1,3]dioxolylcarbonyl, thiophenylmethyl, N-methyl-aza-bicyclo[2.2.2]octyl, aza-bicyclo[2.2.2]octyl, aza-bicyclo[2.2.2]octylmethyl, N-methyl-piperidinyl, N-isopropyl-piperidinyl, N-cyclopropyl-piperidinyl, piperidinyl, N-methyl-pyrrolidinyl, N-ethyl-pyrrolidinylmethyl, pyrrolidinylmethyl, pyrrolidinylethyl, pyrrolidinylpropyl, methylaminoethyl, dimethylaminoethyl and dimethylaminopropyl;

or $R_1$ and $R_2$ taken together with the nitrogen atom to which they are attached form a unsubstituted or at least monosubstituted heterocycle selected from the group consisting of piperazine and diazepane; wherein the substituents are selected from the group consisting of phenyl, fluorophenyl, trifluoromethylphenyl, pyridinyl, thiophenyl, furanyl and methyl.

An example of a compound of formula (I) falling within the scope of the above noted embodiment includes without any limitations the following:

[2-fluoro-5-(1H-indol-5-yl)-phenyl]-[2S-(4-fluoro-phenyl)-4-methyl-piperazin-1-yl]-methanone;

or a pharmaceutically acceptable salt thereof or an optical or stereoisomer thereof.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the compounds disclosed herein can be synthesized according to the following procedures of Schemes 1-10, wherein the X, Y, Z, A, B, D, E, Ar, $R_1$ and $R_2$ are as defined for Formula I unless otherwise indicated.

Schemes 1 and 2 illustrate synthesis of a key intermediate II used in the preparation of compounds of formula I. However, the intermediate aldehyde II can be synthesized by any of the methods known in the art.

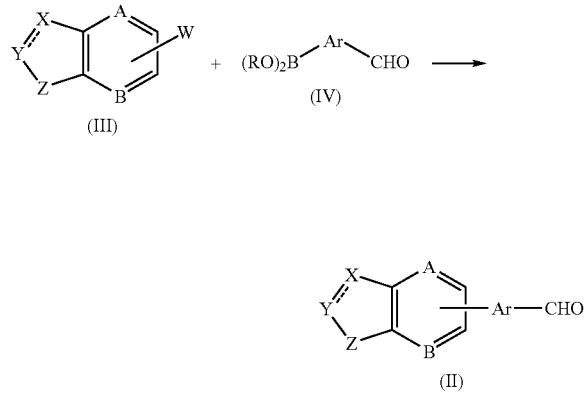

As shown in Scheme 1, the aldehyde II is prepared starting from a compound of the formula III, wherein W is halogen or trifluoromethanesulfonate (triflate). As illustrated, III is reacted with boronic acid or ester of the formula IV (wherein R is hydrogen, $C_{1-4}$alkyl or the two R's taken together with the oxygen atoms to which they are attached form a five or six membered ring) to obtain aldehyde intermediate II. This reaction can be carried out by any of the methods known in the art. For example, such addition reactions are carried out in the presence of a suitable catalyst such as palladium compounds. Examples of palladium compounds suitable for such coupling reactions include tetrakis(triphenylphosphine)palladium chloride or PdCl$_2$(dppf) (dppf=1,1' bis(diphenylphosphino)ferrocene), and the like. The reaction is also generally carried out in the presence of a suitable base, such as for example, cesium carbonate and the like. Further, any groups that may interfere with this addition reaction may need to be protected. For instance, when Z=NH, the nitrogen may be suitably protected before carrying out this coupling reaction. Any of the known nitrogen protecting groups can be employed as long as such protecting groups do not interfere with this reaction. Such protecting groups are described in T. W. Greene, Protective Groups in Organic Synthesis, J. Wiley-Interscience Publication (1999). The reaction can further be carried out in a suitable solvent preferably an organic solvent such as dioxane, dimethylsulfoxide, dimethylformamide, or the like, and at subambient to superambient temperature conditions. Normally, the reaction is carried out at elevated temperatures, for example, at the reflux temperature of the solvent and preferably in an inert atmosphere. The reaction mixture can be heated using conventional methods or alternatively using microwave irradiation. However, as noted above, any of the other known methods can also be used to bring about this coupling reaction to form the aldehyde II.

Alternatively, the aldehyde II can also be prepared using a boronic acid or ester of formula V and an aromatic aldehyde of formula VI as illustrated in Scheme 2. This coupling reaction can essentially be carried out under similar conditions as described above in order to obtain the aldehyde II.

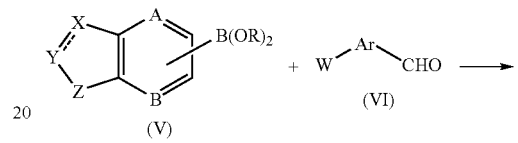

Scheme 3 illustrates preparation of a series of compounds of formula I wherein D is $CH_2$ and $R_2$ is either Ar'$CH_2$ or Ar'CO and wherein Ar' is aryl or heteroaryl as described herein.

In Scheme 3, the intermediate aldehyde II is reacted with a desirable amine under reductive alkylation conditions to form compound of formula VIII. This amine coupling reaction can be carried out using any of the known methods in the art. Generally such reductive amination can be carried out using a reducing agent such as sodiumcyanoborohydride, or sodium triacetoxyborohydride, (NaB(O$_2$CCH$_3$)$_3$H), and the like in a suitable reaction medium, such as tetrahydrofuran or dichloroethane. Alternatively, the reaction of the aldehyde and amine can be carried out in the presence of a dehydrating agent, such as, for example, molecular sieves, in an organic solvent such as methanol, followed by addition of a reducing agent such as sodium borohydride.

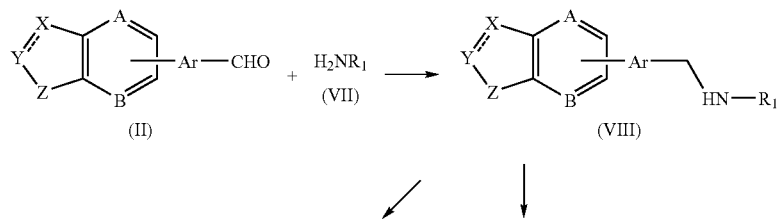

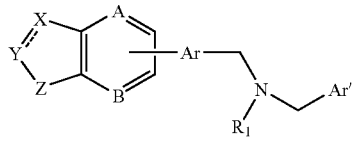
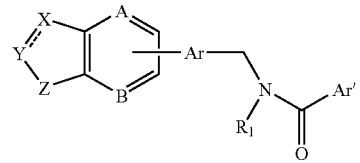

(I); D = CH$_2$ and R$_2$ = Ar'CH$_2$         (I); D = CH$_2$ and R$_2$ = Ar'CO

The intermediate amino compound VIII thus formed is then subjected to another reductive alkylation reaction using a suitable aromatic aldehyde to form compounds of formula I wherein D=CH$_2$ and R$_2$=Ar'CH$_2$. This alkylation reaction can also be carried out under essentially similar conditions as described above. That is, compound of formula VIII is reacted with Ar'CHO in the presence of a suitable reducing agent such as sodium triacetoxyborohydride (NaB(O$_2$CCH$_3$)$_3$H) to form the corresponding compound of formula I. The compound of formula VIII can be reacted with a suitable aromatic carboxylic acid of formula Ar'CO$_2$H or carboxylic acid chloride to form compound of formula I wherein D=CH$_2$ and R$_2$=Ar'CO.

This reaction can again be carried out using any of the methods known in the art. For instance such acylation reactions with carboxylic acid chlorides are carried out in the presence of a suitable base such as triethylamine or diisopropylethylamine in an organic solvent such as dichloromethane. Alternatively reaction of the compound of formula VIII with a carboxylic acid and an amine coupling reagent such as, for example, O-(7-azabenzotriazol-1-yl)-N,N,N',N'-tetramethyluronium hexafluorophosphate (HATU) in the presence of a base such as diisopropylethylamine also affords compounds of formula I.

Scheme 4

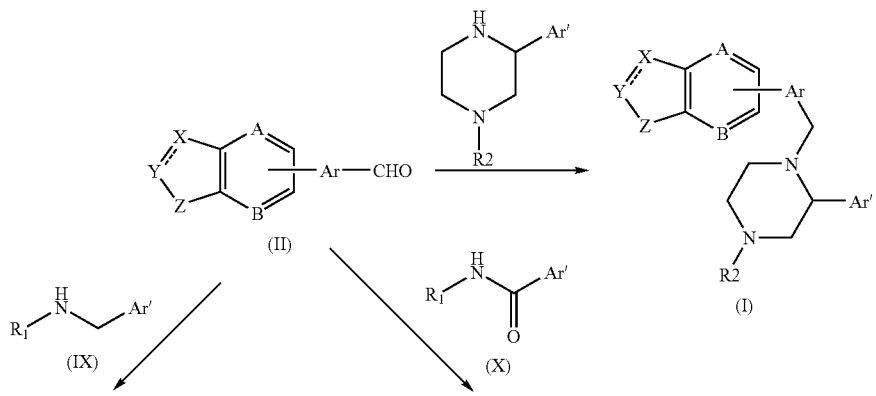

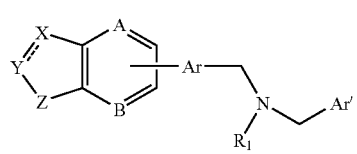
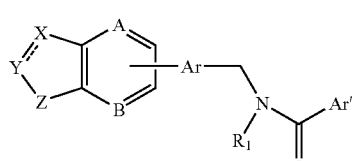

(I); D = CH$_2$ and R$_2$ = Ar'CH$_2$        (I); D = CH$_2$ and R$_2$ = Ar'CO

Alternatively, compounds of formula I of the types shown in Scheme 3 can also be prepared starting from the aldehyde II and a suitable amino compound IX or X as illustrated in Scheme 4. The compound of formula I can also be reacted with cyclic amines such as piperidine derivatives shown to form the corresponding compounds of formula I. Again this amination reaction can be carried out under similar conditions as described above. That is, the aldehyde II is reacted with suitable amine IX or piperidine derivative or suitable amide X in the presence of a suitable reducing agent such assodium triacetoxyborohydride (NaB(O$_2$CCH$_3$)$_3$H) to form the corresponding compounds of formula I.

Scheme 5 illustrates further variation of a synthetic method for the preparation of compounds of formula I. In this approach, halo-aromatic aldehyde of formula VI is first reacted with an amine to form compound of formula XI, which is reacted either with aralkyl halide or aromatic carboxylic acid to form corresponding compounds of formula XII and XIII. The latter compounds are finally reacted with boronic acids or esters of formula V to form the corresponding compounds of formula I wherein D=CH$_2$ and R$_2$ is either Ar'CH$_2$ or Ar'CO.

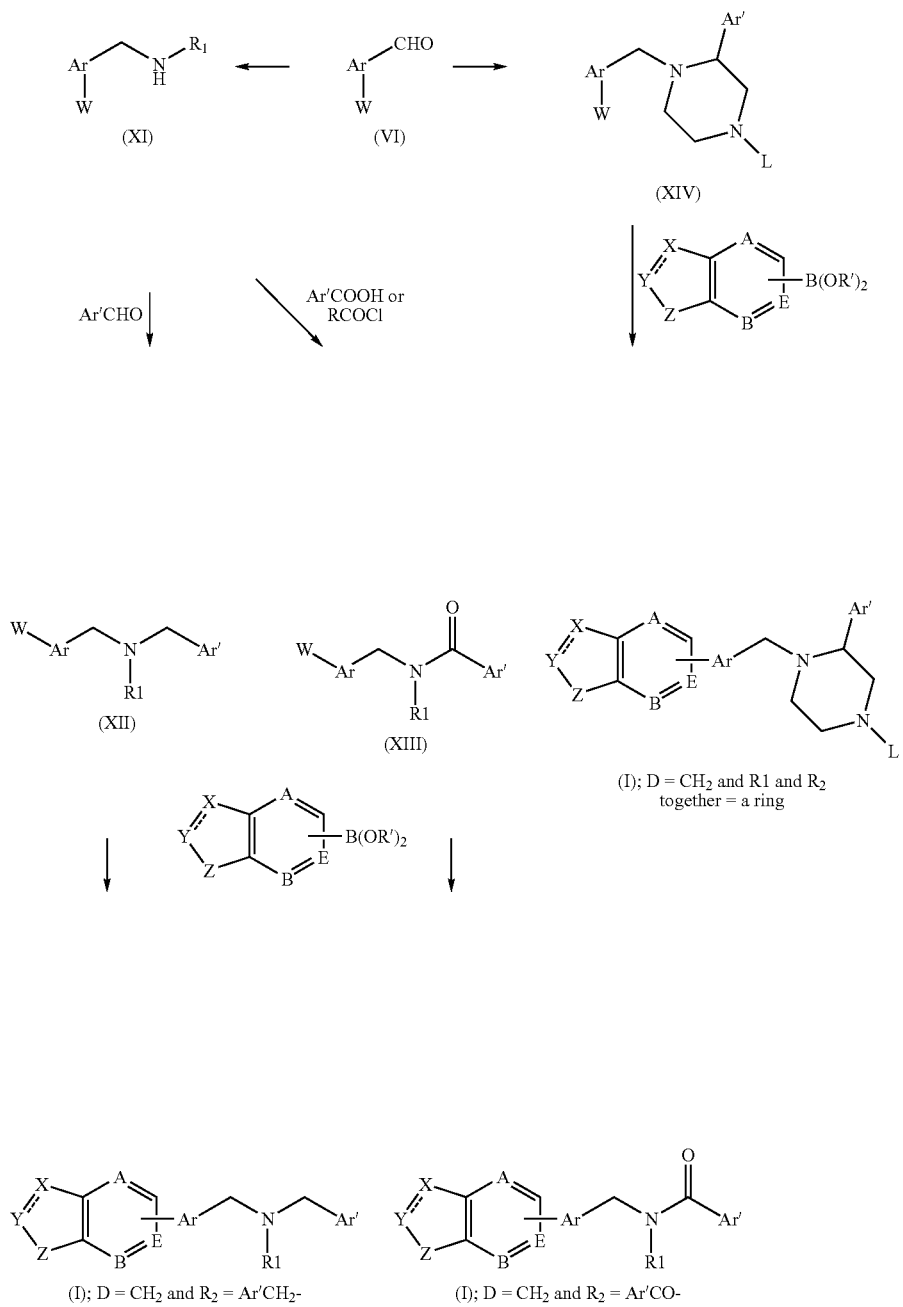

Scheme 5

Similar reaction conditions can be employed for various steps set forth in Scheme 5 as described above. For instance, the reductive amination reaction of the halo-aromatic aldehyde VI with the amine is affected under reductive conditions in the presence of a reducing agent such as sodium triacetoxyborohydride as discussed above for similar reductive amination reactions. The amino compound XI so formed is then subjected to arylation or aroylation by reacting respectively with aralkyl halide such as arylmethylhalide of formula Ar'CH$_2$-halo or an aromatic carboxylic acid such as Ar'CO$_2$H under conditions as described in scheme 4 to obtain the corresponding compounds of formula XII and XIII. Finally, each of which is reacted with the boron compound V to form the corresponding compound of formula I.

The compounds of formula I may also be prepared as outlined in Scheme 6, using the methods described above. For example, the reductive alkylation reaction of the boranyl-aromatic aldehyde XV with an amine is affected under reductive conditions in the presence of a reducing agent such as sodium triacetoxyborohydride as discussed above for similar reductive alkylation reactions. Further treatment of the amine obtained with an aldehyde under similar conditions then provides the boranyl-amine XVI. This boronic acid or ester can then be coupled to an aryl or heteroaryl halide or trifluoromethanesulfonate, in the presence of a suitable organometallic coupling agent as described earlier to afford compounds of formula I.

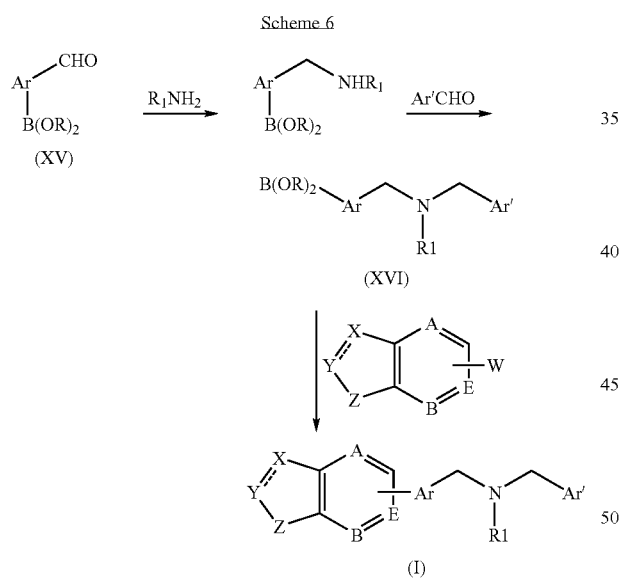

In a similar fashion, as shown in Scheme 7, the boranyl-amine XVII may be prepared by treatment of an amino substituted aryl halide or triflate with a borylating agent such as bis(pinacolato)diboron in the presence of an organometallic coupling agent such as Pd(dppf).DCM in an organic solvent such as dioxane, dimethylsulfoxide or dimethylformamide at elevated temperature. This boronic acid or ester can then be coupled with an aryl halide or trifluoromethanesulfonate under the conditions described above, or for example using fibreCat 1001 in the presence of a phase transfer catalyst such as tetrabutylammonium bromide, a base such as cesium carbonate in a mixture of an organic solvent such as dioxane and water at elevated temperatures.

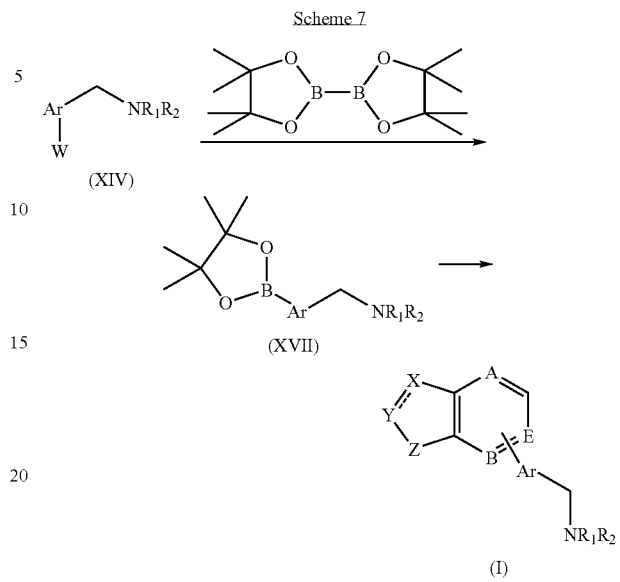

Compounds of formula I may also be prepared as outlined in Scheme 8. Carboxylic acids or esters may be prepared as described for aldehydes in Schemes 1 and 2. Reduction of the acids or esters to the alcohols XIX may be carried out by any number of methods known in the art, including the use of, for example, hydride reducing agents such as lithium aluminum hydride in an appropriate solvent such as diethyl ether or THF. The alcohols so prepared can be activated by transformation into a halide, a mesylate, triflate or nosylate. For example mesylates may be prepared by treating the alcohols with methanesulfonyl chloride or methanesulfonyl anhydride in the presence of a base such as triethyl amine or diisopropylethylamine in an appropriate solvent such as DCM or DCE. Compounds XX can then be transformed to the targets of formula I by treatment with an appropriate amine.

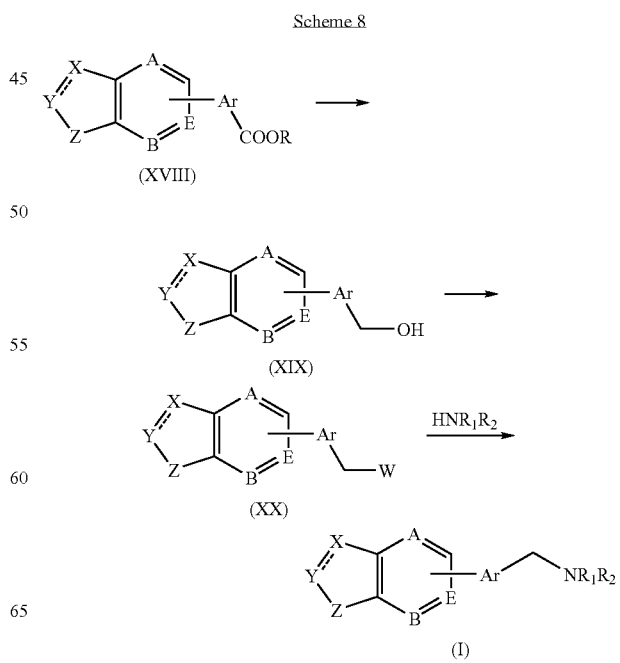

Compounds of formula I in which D═CO may be prepared by methods similar to those described above, replacing a reductive alkylation with an amide forming reaction. For example (Scheme 9), in a method related to the one described in Scheme 5, amidation of a carboxylic acid or carboxylic acid derivative can be accomplished by many known methods. For example amides XXII may be obtained by treatment of carboxylic acids XXI (R″═H) upon treatment with an amine in the presence of a coupling agent, such as HOBT, HOAT or HATU, with a base such as triethylamine or diisopropylamine in an appropriate solvent, for example dimethylformamide or dichloromethane. Subsequent organometallic coupling as described above provides compounds of formula I (D═CO).

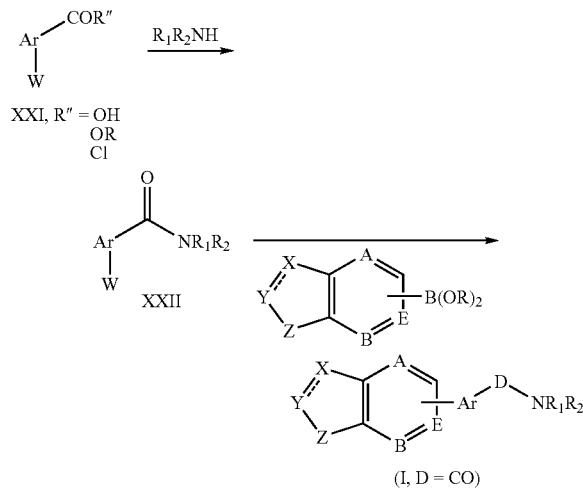

In an alternative approach to the preparation of the compounds of this invention, the heterocyclic ring formed by X, Y, and Z may be prepared by any of a variety of methods known in the art. For example, as shown in Scheme 10, an indole may be prepared from a suitably substituted biaryl or heteroaryl (prepared by the methods described above). Treatment of the nitro compound XXIII with dimethylformamide dimethylacetal in a suitable solvent, such as dimethylformamide, followed by hydrogenation using a Pd or Pt catalyst (for example 10% Pd supported on carbon) provides an compound of formula I where X, Y, and Z are C═C—N and are part of an indole.

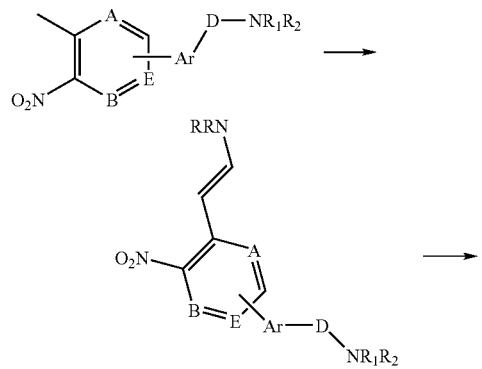

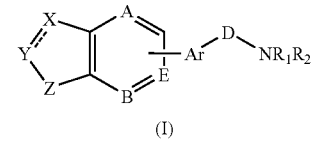

The short acting hypnotic agents as described herein can also be prepared by various known procedures described in the art. For example, preparation of zolpidem is described in U.S. Pat. No. 4,382,938, which is incorporated herein by reference.

The combination of a short and/or long-acting hypnotic agent with a sleep aid allows to obtain beneficial effects on the sleep of the patient and that this effect is greater to the one when each of these two hypnotic agents are taken separately.

In accordance with the first aspect of the invention, the short-acting hypnotic agent and compound of formula (I) are released immediately. The two agents then appear in the plasma according to their respective pharmacokinetic characteristics. Generally, the short-acting hypnotic agent appears in the plasma before the long-acting hypnotic agent. Further, in this aspect of the invention, each agent develops its mechanism of action independent of each other, providing a synergistic effect between the two agents.

In yet another aspect of the invention, the short-acting hypnotic agent is released with a delay and the sleep aid, such as compound of formula (I), is released immediately. According to this aspect of the invention, the action of the short-acting hypnotic agent is increased with increasing residence time in the plasma. Thus, the two agents can act at the same time, also with a synergistic effect.

Examples of short-acting hypnotic agents useable within the framework of the invention are in particular the modulators of the GABA-A receptors, the benzodiazepines, the melatonin derivatives, the agonists of the melatonin receptors. For example, the short-acting hypnotic agent can be chosen from among, in particular, zolpidem, zopiclone, eszopiclone, zaleplon, melatonin, ramelteon, triazolam, etizolam, brotizolam and indiplon, as well as derivatives and/or mixtures thereof.

Examples of long-acting hypnotic agents and/or the sleep aids useable within the framework of the invention are in particular the antagonists of the 5HT2A receptors, the modulators of the GABA-A receptors, benzodiazepines and the modulators of calcium ions. For example, the long-acting hypnotic agent and/or the sleep aids can be chosen from among, in particular, the compound of formula (I), temazepam, clonazepam, gaboxadol, pregabaline, as well as derivatives and/or mixtures thereof.

The short or long-acting hypnotic agents and/or the sleep aids described above can comprise one or more asymmetric carbon atoms. They can thus exist in the form of enantiomers or diastereoisomers. These enantiomers or diastereoisomers, as well as mixtures thereof, including the racemic mixtures, are part of the invention.

The short or long-acting hypnotic agents and/or sleep aids described above can also exist in the form of free bases or acids as well as their pharmaceutically acceptable salts. Such salts are also part of the invention. These salts can be prepared with pharmaceutically acceptable acids or bases following the procedures well known in the art.

The short or long-acting hypnotic agents and/or sleep aids described above can also exist in the form of hydrates or solvates, i.e., in a form of associations or combinations with one or more molecules of water or a solvent. Such hydrates and solvates are also part of the invention.

According to one embodiment of the invention, the combination comprises zolpidem hemitartarate as short-acting hypnotic agent and the compound of formula (I) as a sleep aid.

According to another aspect, the invention concerns pharmaceutical compositions comprising, as active principle, at least one short-acting hypnotic agent and at least one long-acting hypnotic agent and/or a sleep aid. The pharmaceutical compositions of the invention comprise an effective dose of at least one short-acting hypnotic agent and at least one long-acting hypnotic agent and/or a sleep aid, or a pharmaceutically acceptable salt of these agents, a hydrate or solvate of said agents, as well as at least a pharmaceutically acceptable excipient.

The excipients are chosen according to the desired pharmaceutical form and administration mode, from among the usual excipients known to a person skilled in the art. The short or long-acting hypnotic agents and the sleep aids can be chosen from among the ones described above.

The unit-dose packages of appropriate administration comprise the forms: via oral administration, such as tablets, particularly multi-layer tablets, coated tablets, tablets with a core, soft or hard capsules, powders, granules and oral solutions or suspensions, sublingual or by mouth administration forms.

In another embodiment of this invention, the long-acting hypnotic agent and/or the sleep aid and the short-acting hypnotic agents present in the composition according to the invention, are released immediately.

In yet another embodiment of this invention, the long-acting hypnotic agent and/or the sleep aid present in the composition according to the invention is immediately released and the short-acting hypnotic agent is released with a delay.

The immediate-release entity can be a unit with immediate-release of a pharmaceutical product such as, for example, a tablet or a capsule with immediate-release, or several of these units in the form of tablet formulated in a capsule; the immediate-release system of one tablet; an immediate-release layer incorporated in a multi-layer tablet; one or more coating layers in a tablet or pellet.

The delayed release entity can be a unit with delayed release of a pharmaceutical product such as, for example, a delayed-release tablet or capsule; or several of these units formulated in a capsule; a delayed-release layer incorporated in a multi-layer tablet; a delayed-release core or a coating layer incorporated in a tablet with several coats; delayed-release pellets inside a disintegrating tablet.

The long-acting hypnotic agent and/or the sleep aid, and the short-acting hypnotic agent can be formulated according to the invention in one single pharmaceutical composition, or, alternatively, in separate pharmaceutical compositions for a simultaneous, separate, or sequential administration.

Orally, the dose of active principle present in a composition according to the invention varies from about 0.1 to about 30 mg of long-acting hypnotic agent or from about 0.1 to about 30 mg of sleep aid such as compound of formula (I), and about 0.1 to about 30 mg of short-acting hypnotic agent.

For example, a composition according to the invention contains about 0.2 to about 15 mg, in particular from 1 to 10 mg compound of formula (I), and about 0.2 to about 20 mg, in particular from 1 to 10 mg zolpidem in base form.

Particular cases can exist where higher or lower dosages are appropriate; such dosages are not outside the scope of the invention. According to the usual practice, the appropriate dosage for each patient is determined by the physician, depending on the mode of administration, the weight, and the response of said patient.

In an embodiment of the compositions according to the invention consists in a capsule comprising one or more immediate-release tablets containing the short-acting hypnotic agent and one or more immediate-release tablets containing the long-acting hypnotic agent and/or the sleep aid.

In another embodiment of the compositions according to the invention consists in a capsule comprising one or more delayed-release tablets containing the short-acting hypnotic agent and one or more immediate-release tablets containing the long-acting hypnotic agent and/or the sleep aid.

Another embodiment of the compositions according to the invention consists in a capsule comprising a mixture of immediate-release pellets of the short-acting hypnotic agent and of immediate-release pellets of the long-acting hypnotic agent and/or the sleep aid.

Yet another embodiment of the compositions according to the invention consists in a capsule comprising a mixture of immediate-release pellets of the short-acting hypnotic agent and of immediate-release pellets of the long-acting hypnotic agent and/or the sleep aid.

In a further embodiment of the compositions according to the invention consists in a tablet comprising immediate-release pellets of the short-acting hypnotic agent and the long-acting hypnotic agent and/or the sleep aid.

Yet another embodiment of the compositions according to the invention consists in a tablet comprising delayed-release pellets of the short-acting hypnotic agent and of immediate-release pellets of the long-acting hypnotic agent and/or the sleep aid.

Another embodiment of the compositions according to the invention consists in an enteric-coated, delayed-release tablet comprising immediate-release pellets of the long-acting hypnotic agent and/or the sleep aid, and of immediate-release pellets of the short-acting hypnotic agent.

Another embodiment of the compositions according to the invention consists in a dry-coated tablet, characterized in that it comprises a delayed-release inner core containing the long-acting hypnotic agent and/or the sleep aid, and in that the immediate-releasing coating layer contains the long-acting hypnotic agent and/or the sleep aid.

In another aspect of this invention, a specific disease, a disorder or a condition that can be treated with the combination and/or the pharmaceutical composition comprising the combination of this invention include, without any limitation a wide variety of sleep disorders. As already noted hereinabove, specific sleep disorders that can be treated in accordance with this invention include without any limitation insomnia, primary insomnia, sleep maintenance insomnia, insomnia related to another mental disorder, substance induced insomnia and obstructive sleep apnea.

The compositions according to the invention can be prepared according to the methods known by a person skilled in the art.

Thus, the capsules containing one or more reduced-size, immediate-release tablets containing the long-acting hypnotic agent and/or the sleep aid, and one or more reduced-size, immediate-release tablets containing the short-acting hypnotic agent can be prepared as follows.

The immediate-release tablets can be prepared with direct compression of active principle mixtures in the base form or salts with diluents such as microcrystalline cellulose, mannitol, sorbitol, lactose. Other excipients, such as disintegrators or lubricants, can be added. The choice between these functional excipients, as well as these diluents, is well known by a person skilled in the art.

According to another embodiment, tablets can be prepared by granulation with water or solvents of a mixture of one or more of the active principles mixed with diluents, appropriate disintegrating agents and polymers, then calibration and drying of the obtained pellet, addition of lubricating agent, followed by a compression with a compression machine. Various methods of tablet making are generally described in literature, such as, for example, B. B. Sheth, F. J. Bandelin, R. J F. Shangraw, Compressed tablets, in Pharmaceutical dosage forms: Tablets, Vol 1, published by H. A. Lieberman and L Lachman, Dekker N, Y. (1980).

Capsules containing one or more reduced-size, immediate-release tablets containing the long-acting hypnotic agent and/or the sleep aid, and one or more reduced-size, delayed-release tablets containing the short-acting hypnotic agent can be prepared following the known procedures in the art.

Delayed-release tablets containing the short acting hypnotic agent can be prepared by coating the immediate-release tablets, such as described above, with a polymer coating having a limited diffusion. Such polymers can be chosen among ethylcellulose copolymers as well as methyl methacrylate polymers, such as commercialized products named Eudragit TM RS®, Eudragit TM RL®, Eudragit TM NE®, all of which are commercially available from Rohm Pharma.

Coating methods can consist in pulverization of a polymer solution on the tablets, in a coating machine or a fluidized bed device. The solvent that can be employed is either organic or aqueous, depending on the nature of the polymer used. Coating methods are described, in particular in J. M. Bakan, Microencapsulation, in L. Lachman, H. Lieberman and J. L. Kanig (Eds), The Theory and Practice of Industrial Pharmacy, Lea & Febinger, Philadelphia, USA, 1986; J. M. Mc Ginity, Aqueous Polymer Coatings for Pharmaceutical Dosage Forms, Dekker N.Y., 1989.

Delayed-release tablets can also be prepared with the incorporation of excipients forming the matrix in the formulation, with no disintegrating agent. Examples of excipients, forming the matrix are the hydrophilic polymers, in particular hydroxypropylmethylcellulose, hydroxymethylcellulose, hydroxyethylcellulose, which expand when in contact with aqueous liquids and which can control the release of the active principle through the expanded polymeric network. Such excipients are used in a quantity in percentage weight of about 10% to about 40% of the total weight of the tablet.

Delayed-release tablets can also be formulated, in the case of basic active principles, with a pharmaceutically acceptable organic acid, chosen among those indicated hereafter, in order to maintain its dissolution in the neutral pH conditions in the small intestine. Examples of organic acids useable are among maleic, tartaric, malic, fumaric, lactic, citric, adipic and succinic acid.

Capsules containing a mixture of immediate-release pellets of the long and short-acting hypnotic agent and/or a sleep aid can be prepared as follows. Immediate-release pellets of the long and short-acting hypnotic agent and/or a sleep aid can be prepared by precipitating the active principle in suspension in water with, for example, hydroxypropylmethylcellulose or in an organic solvent such as ethanol or another appropriate polymer acting as a binder on a spherical granule. A coating device with fluidized bed is generally used. Particles can be agglomerated in order to form spherical granules or pellets, in a high-speed granulator-mixer or a rotary agglomerator with fluidized bed. Such methods are described in K. W. Olson, A. M. Mehta, Int. J. Phar. Tech & Prod. Mfr. 6 18-24, 1985. Pellets can generally be prepared by mass extrusion or by melting followed by spheronization, as described, for example, in C. Vervaet, L. Baert & J. P. Remon, Int. J. Pharm. 116 (1995) 131-146.

The excipients used are typically those having good plastic qualities such as microcrystalline cellulose, mannitol. Small quantities of binder are generally added. Surfactant agents, such as sodium dodecyl sulfate can also be incorporated in order to facilitate the extrusion.

Capsules containing a mixture of immediate-release pellets of long-acting hypnotic agent and/or a sleep aid, and delayed-release pellets of short-acting hypnotic agent can be prepared as follows. Immediate-release pellets can be prepared as described above. Delayed-release pellets can contain, in the case of basic active principles, a pharmaceutically acceptable organic acid or an acid salt of such organic acid, for maintaining the local pH inside the pellet during its dissolution under neutral pH in the small intestine.

Alternately, pellets can be coated with pH sensitive membrane, containing a polymer soluble under neutral pH and impermeable to an acid pH, such as, for example, the product Eudragit TM S®, which allows a permeation of the active principle at a pH higher than about 5, for compensating the reduced solubility of the active principle at low pH levels.

Tablets containing several immediate-release pellets of long-acting hypnotic agent and/or a sleep aid and short-acting hypnotic agent can be prepared as follows. The different pellets can be immersed in a matrix where the matrix itself can contain one of the hypnotic agents. Then tablets disintegrate when they are in contact with a fluid, releasing quickly the active principle, or immediate-release pellets, or from the coating of immediate-release pellets.

Tablets containing one or several immediate-release pellets of long-acting hypnotic agent and/or a sleep aid and one or several delayed-release pellets of short-acting hypnotic agent can be prepared as follows.

1) The tablet can consist in a mixture of immediate-release pellets and delayed-release pellets containing the active principle, immersed in a matrix which does not contain an active principle.

2) Alternatively, pellets containing the two hypnotic agents and/or sleep aids can be immersed in a matrix containing itself one of the two therapeutic agents.

According to another embodiment of this invention, delayed-release pellets can be coated with a layer containing the active principle and excipients, allowing an immediate-release from this coating layer, immersed in a matrix with no active principle. The matrix surrounding the pellets is formulated in order that the compression in tablets does not interfere with the membrane integrity surrounding the pellets. Tablet disintegrates when it is in contact with a fluid, releasing quickly the long-acting hypnotic agent and/or a sleep aid, from the matrix or immediate-release pellets, or from the coatings of immediate-release pellets and by releasing then the short-acting hypnotic agent, from delayed-release pellets.

The pharmaceutical composition of the invention can also be found in the form of a multilayer tablet. Such a multilayer tablet comprises:

One or several layer with immediate-release, each one containing a dose of long-acting hypnotic agent and/or a sleep aid, and eventually a dose of short-acting hypnotic agent;

One or more layers with delayed release, each one containing a dose of short-acting hypnotic agent; and Eventually a supplementary layer which does not contain any active principle but contains hydrophilic polymers such as the cellulose derivative, for example, hydroxypropylcellulose, hydroxyethylcellulose, hydroxymethylcellulose, or soluble diluents, such as, lactose, sorbitol, mannitol, one or more other hydrophilic polymers and/or one or more other soluble excipients, this layer modulating the active principle release from the delayed release layer. Each layer contains eventually other excipients, in order to allow a good compression, lubrication, and binder of the tablet.

Another embodiment of this invention consists in a core containing the short-acting hypnotic agent, eventually with a pharmaceutically acceptable organic acid. The core is coated with a polymer layer containing the long-acting hypnotic agent and/or a sleep aid that is quickly or immediately released in contact with fluids, while the short-acting hypnotic agent is released from the core. Eventually, the core and the coating layer can be formulated in order to allow a release in the colon. Each constituent of the multiple coated tablet can contain other excipients, to allow a good compression, lubrication and binder. Preparation processes of multiplayer tablets and multiple coating tablets are described in particular in W. C. Gunsel, Compression coated and layer tablets in pharmaceutical dosage forms: tablets, Vol 1, published by H. A. Lieberman and L. Lachman, Dekker N.Y. (1980).

This invention is further illustrated by the following examples which are provided for illustration purposes and in no way limit the scope of the present invention.

EXAMPLES

General

Examples 1 to 4 show preparation of a few of the specific compounds of formula (I). Example 5 shows how to use the combination of this invention and Examples 6 to 16 provide methods for the preparations of the pharmaceutical compositions of the combination of the invention with a compound of formula (I) and a short acting hypnotic.

Reactions generally are run under an inert atmosphere. All commercial chemicals and solvents are reagent grade and were used without further purification unless otherwise specified. All reactions except those in aqueous solution or otherwise noted were carried out with the use of standard techniques for the exclusion of moisture. Flash chromatography was carried out using silica gel 60 (35-70 um) according to the literature procedure (Still, W. C.; Kahn, M; Mitra, A. *J. Org. Chem.* 1978 43, 2923) or a variation of this method using commercially available silica gel cartridges (for example Isco Redi Sep) Reactions using focused or single mode microwave irradiation were performed on instruments from CEM Corporation or Personal Chemistry. The $^1$H NMR spectra are run at 300 MHz or 400 MHz on a Gemini 300, Varian VXR 300 or Varian Inova-400 spectrometer and are determined in a deuterated solvent, such as DMSO-D$_6$ or CDCl$_3$ unless otherwise noted. Chemical shifts values are indicated in parts per million (ppm) with reference to tetramethylsilane (TMS) as the internal standard. Liquid chromatography with mass spectral analysis (LC/MS) is recorded on a Platform LC Mass Spectrometer with electrospray source operating in positive and negative ion mode and an HP1100 with inline HP1100 DAD detection and SEDEX ELS detection using a Waters XTerra MS C18 3.5 µm 4.6×30 mm or a Phenomenex Luna C18(2) 30×4.6 mm column eluting with 0.1% formic acid in water/acetonitrile (short LC/MS), or a Finnigan TSQ700 Mass Spectrometer with electrospray source operating in positive ion mode and an HP1050 system with inline HP1050 Single Wavelength UV detector at 254 nm using a Higgins Clipeus C18 5 µm 100×3.0 mm column eluting with 0.1% formic acid in water/acetonitrile (long LC/MS), or a Micromass LCTAPI LC-TOF (time of flight) Mass Spectrometer and Masslynx Data System. Ionization mode=electrospray (esi), values are determined for the protonated molecular ions (M$^+$+1) using a Synergi 2U HYDRO-rP 20×4 mm column, eluting with 0.1% trifluoroacetic acid (TFA) in water/acetonitrile (method 3)

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "L" refers to liters, "mL" or "ml" refers to milliliters, "µL" refers to microliters, "gal" refers to gallons, "° C." refers to degrees Celsius, "R$_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "dppf" refers to 1,1' bis(diphenylphosphino)ferrocene, "THF" refers to tetrahydrofuran, "DMF" refers to dimethylformamide, "DMAP" refers to dimethylaminopyridine; "DMSO" refers to dimethylsulfoxide; "NMP" refers to 1-methyl-2-pyrrolidinone, "DCM" refers to dichloromethane, "DCE" refers to dichloroethane, "EtOAc" refers to ethyl acetate, "MeOH" refers to methanol, "HOAc" or "AcOH" refers to acetic acid, "H$_2$O" refers to water; "NaOH" refers to sodium hydroxide, "HCl" refers to hydrochloric acid, "Cs$_2$CO$_3$" refers to cesium carbonate, "MgSO$_4$" refers to magnesium sulfate, "Na$_2$SO$_4$" refers to sodium sulfate, "brine" refers to a saturated aqueous sodium chloride solution, "HATU" refers to O-(7-azabenzotriazol-1-yl)-1,1,3,3-tetramethyluronium hexafluorophosphate, "M" refers to molar, "mM" refers to millimolar, "µM" refers to micromolar, "mM" refers to nanomolar, "N" refers to normal, "TLC" refers to thin layer chromatography, "HPLC" refers to high performance liquid chromatography, "HRMS" refers to high resolution mass spectrum, "L.O.D." refers to loss on drying, "µCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets; br=broad; LC=liquid chromatograph; MS=mass spectrograph; ESI/MS=electrospray ionization/mass spectrograph; RT=retention time; M=molecular ion.

Example 1

N-Benzyl-N-[3-(1H-indol-5-yl)-benzyl]-N',N'-dimethyl-ethane-1,2-diamine

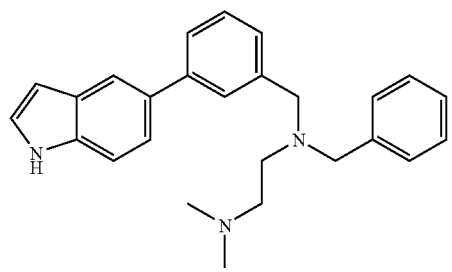

Step 1: 3-(1H-Indol-5-yl)-benzaldehyde: A mixture of 5-bromo-indole (8.7 g, 44.4 mmol), 3-formylbenzeneboronic acid (10 g, 66.7 mmol), cesium carbonate in water (2M, 88.8 mL, 178 mmol) in 450 mL of dioxane was degassed (evacuate in vacuo and pressurize with nitrogen, 3 times) $PdCl_2(dppf)$ .DCM (1.1 g, 1.3 mmol) was added and the mixture degassed one more time as described above. The resulting mixture was heated at 100° C. for 3 h, then it was allowed to cool to room temperature and partitioned between diethyl ether and water. The aqueous phase was extracted with diethyl ether and the combined organic phases were washed with water, brine, dried over $MgSO_4$, filtered and evaporated to give the crude product. Chromatography on silica gel (elution with ethyl acetate/heptane) afforded 5.6 g of the desired product.

Step 2: N-Benzyl-N-[3-(1H-indol-5-yl)-benzyl]-N',N'-dimethyl-ethane-1,2-diamine: Sodium triacetoxyborohydride (480 mg, 2.3 mmol) was added to a solution of 3-(1H-indol-5-yl)-benzaldehyde (250 mg, 1.1 mmol) and N'-benzyl-N,N-dimethyl-ethane-1,2-diamine (600 mg, 3.4 mmol) and acetic acid (204 mg, 3.4 mmol) in 8 mL of tetrahydrofuran. The mixture was stirred at ambient temperature overnight, and then it was diluted with ethyl acetate, and neutralized with the careful addition of saturated sodium bicarbonate solution. The layers were separated and the organic phase was treated with polystyrene supported isocyanate resin (1.49 mmol/g, 1.7 g) for 2 h. The mixture was filtered and the filtrate was washed with 1M sodium carbonate solution. The aqueous phase was extracted into ethyl acetate, and the combined organic phases were dried over magnesium sulfate, filtered and concentrated to leave 290 mg of the title compound. LC/MS (short method): retention time, 2.61 min; (M+H)=384.50.

$^1$H NMR (400 MHz, chloroform-D) δ ppm: 2.20 (s, 6 H) 2.49-2.55 (m, 2 H), 2.65-2.68 (m, 2 H) 3.66 (s, 2 H) 3.69 (s, 2 H) 6.61 (br s, 1 H) 7.21-7.26 (m, 3 H) 7.28-7.34 (m, 3 H) 7.35-7.41 (m, 3 H) 7.45 (s, 2 H) 7.52 (d, 1 H, J=7.6 Hz), 7.64 (s, 1 H) 7.85 (s, 1 H) 8.26 (s, 1 H).

Example 2

5-{4-Fluoro-3-[2S-(4-fluoro-phenyl)-piperazin-1-ylmethyl]-phenyl}-1H-indazole

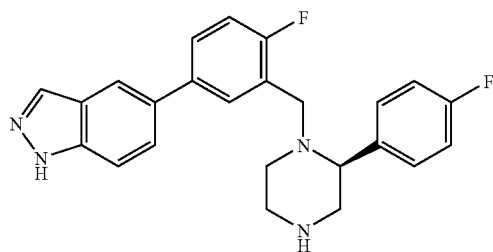

Step 1: 2S-(4-Fluorophenyl)-piperazine: A solution of ethylene diamine (7.4 g, 123.5 mmol) in ethanol (100 mL) was added dropwise over 15 minutes to a stirring solution of 4-fluoroglyoxal (21.0 g, 123.5 mmol) in ethanol (300 mL) and the reaction was left for 4 hours. Sodium borohydride (23.5 g, 622 mmol) was added and the mixture was stirred overnight at room temperature. Water (200 mL) was added and the mixture was stirred for 1 hour after which the majority of the ethanol was removed in vacuo. The concentrated solution was extracted with DCM (4×100 mL) and the combined extracts were combined, washed with brine and dried over $Na_2SO_4$. The solvent was removed in vacuo to yield a pale yellow solid (19.0 g, 86%). 8.8 g of this material was dissolved in methanol (60 mL) and added to a solution of N-acetyl-L-leucine (16.5 g, 95.2 mmol) in methanol (100 mL). Ethyl acetate (550 mL) was added and the mixture was left at room temperature overnight. The precipitate was filtered and dried to give a solid (9.0 g) which was taken up in 4M NaOH aq. (100 mL) and extracted with DCM (4×100 mL). The combined extracts were combined, washed with brine and the solvent was removed in vacuo to yield a solid (3.1 g). This solid was re-crystallized from EtOAc to yield 2.23 g of the S enantiomer (the title compound). The enantiomeric excess was determined by chiral chromatography employing the following chiral chromatographic conditions: Column: Phenomenex Chirex (S)-ICR 250×4.6 mm; solvent: n-heptane:ethanol [80:20]+0.3% TFA; L=254 nm, flow rate=1 mL/min, UV sensitivity=0.1 AUF; ~1 mg of compound in 1 mL of n-heptane:ethanol [75:25] using authentic chiral compounds and racemate as reference.

Step 2: 3S-(4-Fluorophenyl)-piperazine-1-carboxylic acid tert-butyl ester: 2S-(4-Fluorophenyl)-piperazine (3.75 g, 20.83 mmol) was dissolved in dichloromethane and cooled to 0° C. A solution of di-tert-butyl-dicarbonate (4.77 g, 21.87 mmol) in 10 mL of dichloromethane was added and the reaction was left at 0° C. for one hour. The solvent was removed in vacuo to yield a crystalline white solid (5.85 g).

Step 3: 5-Bromo-indazole-1-carboxylic acid tert-butyl ester: Di-tert-butyldicarbonate (11.4 g, 52.21 mmol), triethylamine (6.27 g, 62.16 mmol) and 4-(N,N-dimethylaminopyridine (304 mg, 2.49 mmol) were added sequentially to a solution of 5-bromoindazole (9.8 g, 49.73 mmol) in tetrahydrofuran at room temperature. The mixture was stirred at room temperature for 71.5 h and then it was heated at reflux for 16 h. The volatiles were removed in vacuo and the residue was dissolved in dichloromethane and washed with brine, dried over magnesium sulfate, filtered and concentrated to leave the crude product. Chromatography (elution with diethyl ether/heptane) gave 13.98 g of the title compound. LC: Retention time, 3.93 min.

Step 4: 5-(4-Fluoro-3-formylphenyl)-indazole-1-carboxylic acid tert-butyl ester: A mixture of 5-bromo-indazole-1-carboxylic acid tert-butyl ester (3.37 mmol), 2-fluoro-4-(4,4,5,5-tetramethyl-[1,3] dioxolan-2-yl)-benzaldehyde (1.01 g, 4.04 mmol)) $PdCl_2(dppf)$.DCM (27 mg, 0.03 mmol) in 16 mL of dioxane was degassed (evacuate in vacuo and pressurize with argon, three times); cesium carbonate in water (2M, 6.73 mL, 13.46 mmol) was added and the mixture degassed three more times as described above. The resulting mixture was heated at 85° C. for 6 h, then it was allowed to cool to room temperature and left overnight. The mixture was diluted with dichloromethane and washed with brine. The aqueous phase was extracted with dichloromethane and the combined organic phases were washed with brine, dried over $MgSO_4$, filtered and evaporated to give crude product. Chromatography on silica gel (elution with diethyl ether/heptane) gave 820 mg of the title compound.

Step 5: 5-{4-Fluoro-3-[2S-(4-fluoro-phenyl)-piperazin-1-ylmethyl]-phenyl}-1H-indazole: 3S-(4-Fluorophenyl)-piperazine-1-carboxylic acid tert-butyl ester (150 mg, 0.54 mmol) and 5-(4-fluoro-3-formylphenyl)-indazole-1-carboxylic acid tert-butyl ester (210 mg, 0.62 mmol) was dissolved in DCE (5 mL) and glacial acetic acid was added (32 mg, 0.54 mmol) followed by sodium tris-acetoxyborohydride (341 mg, 1.6 mmol). The reaction was stirred overnight at room temperature. Dichloromethane was added and the mixture was washed with water and brine and dried over $Na_2SO_4$. The solvent was removed in vacuo to give the crude product.

Chromatography (elution with methanol/dichloromethane) provided 200 mg of product. This was treated with 15 mL of 95% aqueous TFA for 1.5 h. The volatiles were removed in vacuo and residue triturated with diethyl ether (3×) leaving 70 mg of product. LC/MS (long run): Retention time, 6.14 min; (M+H)=405.

$^1$H NMR (400 MHz, methanol-D$_4$) δ ppm: 2.57 (td, J=12.64, 2.64 Hz, 1 H) 3.09-3.36 (m, 5 H) 3.41 (d, J=13.6 Hz, 1 H) 3.67 (dd, J=11.43, 3.08 Hz, 1 H) 3.77 (d, J=13.6 Hz, 1 H) 7.10-7.21 (m, 3 H) 7.53-7.62 (m, 6 H) 7.94 (t, J=1.32 Hz, 1 H) 8.11 (s, 1 H).

Example 3

N-[5-(1H-Benzotriazol-5-yl)-2-fluoro-benzyl]-N-(1-ethyl-pyrrolidin-2S-ylmethyl)-4-fluoro-benzamide

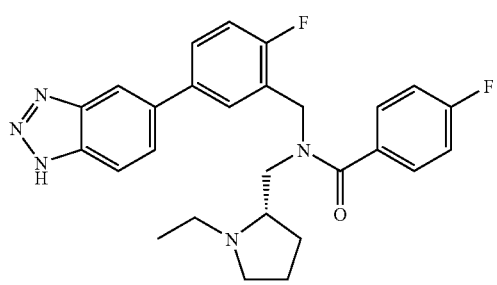

Step 1: (1-Ethyl-pyrrolidin-2S-ylmethyl)-[2-fluoro-5-(1-trityl-1H-benzotriazol-5-yl)-benzyl]-amine: A mixture of 2-fluoro-5-(1-trityl-1H-benzotriazol-5-yl)-benzaldehyde (368 mg, 0.76 mmol), (S)-(+)-1-ethyl-2-aminomethylpyrrolidine (120 mg, 0.83 mmol) and molecular sieves in 10 mL of methanol was stirred at ambient temperature for 3 h. The mixture was cooled to −78° C., and sodium borohydride (72 mg, 1.9 mmol) was added and the mixture was allowed to warm to room temperature and stirred overnight. The volatiles were removed in vacuo and the residue was diluted with dichloromethane and washed with water. The aqueous phase extracted with dichloromethane, and the combined organic phases were washed with brine, dried over magnesium sulfate, filtered and concentrated to leave the crude product. Chromatography (elution with methanol/dichloromethane) gave 255 mg of product.

Step 2: N-(1-Ethyl-pyrrolidin-2S-ylmethyl)-4-fluoro-N-[2-fluoro-5-(1-trityl-1H-benzotriazol-5-yl)-benzyl]-benzamide. HATU (122 mg, 0.32 mmol) was added to a solution of (1-ethyl-pyrrolidin-2-ylmethyl)-[2-fluoro-5-(1-trityl-1H-benzotriazol-5-yl)-benzyl]-amine (127 mg, 0.21 mmol), 4-fluorobenzoic acid (45 mg, 0.32 mmol) and diisopropylethylamine (82 mg, 0.64 mmol) in 1 mL of dimethylformamide, and the resulting mixture stirred at ambient temperature overnight. The mixture was diluted with dichloromethane, and washed with saturated sodium bicarbonate solution and brine, dried over magnesium sulfate, filtered and concentrated to leave the crude product. Chromatography (elution with methanol/dichloromethane) provided 98 mg of product. LC/MS: Retention time, 3.39 min; (M+H)=718.57.

Step 3: N-[5-(1H-Benzotriazol-5-yl)-2-fluoro-benzyl]-N-(1-ethyl-pyrrolidin-2S-ylmethyl)-4-fluoro-benzamide: N-(1-Ethyl-pyrrolidin-2-ylmethyl)-4-fluoro-N-[2-fluoro-5-(1-trityl-1H-benzotriazol-5-yl)-benzyl]-benzamide (143 mg, 0.2 mmol) in 4 mL of methanol and 2 mL of 4M HCl in dioxane was stirred at room temperature for 24 h. The solvent was removed in vacuo and the residue purified by HPLC. The material obtained was treated with hydrochloric acid to leave 100 mg of the title compound. LC/MS (long run): Retention time, 5.64 min; (M+H)=476.

$^1$H NMR (400 MHz, methanol-D$_4$) δ ppm: 1.29-1.46 (m, 3 H) 1.86-1.99 (m, 1 H) 2.04-2.19 (m, 2 H) 2.31 (ddd, J=13.19, 7.03 Hz, 1 H) 3.08-3.28 (m, 2 H) 3.48 (br s, 1 H) 3.68-3.78 (m, 2 H) 3.85 (dd, J=14.73, 5.49 Hz, 1 H) 4.02 (dd, J=14.73, 5.49 Hz 1 H) 4.76-4.95 (m, 2 H) 7.18-7.32 (m, 3 H) 7.51-7.64 (m, 3 H) 7.71-7.79 (m, 2 H) 7.98 (d, J=8.57 Hz, 1 H) 8.06 (s, 1 H).

Example 4

6-{5-[2S-(4-Fluorophenyl)-4-methylpiperazine-1-ylmethyl]-furan-3-yl}-3H-benzoxazol-2-one

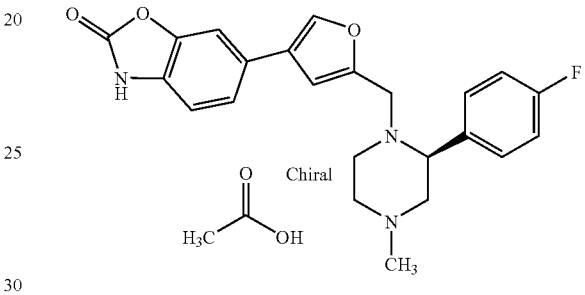

Step 1: 6-Bromo-3H-benzoxazol-2-one: To a mixture of 3H-benzooxazol-2-one (20 g, 0.15 mol) in DCM (500 mL) was added bromine (8.34 mL, 0.16 mol). After stirring at room temperature for 19.5 h, the orange precipitate that had formed was filtered off and washed with DCM until the orange color was washed out. The filtrate was concentrated to approximately 33% of its original volume and filtered and washed as before. The combined solids weighed 28.36 g. $^1$H NMR indicated the product was clean albeit contained ca. 8-9% starting material meaning the true yield of product was 26.72 g, 84%.

Step 2: 6-Bromo-3-trityl-benzoxazol-2-one: To a solution of 6-bromo-3H-benzoxazol-2-one (15 g; ca. 0.07 mol, containing 8-9% 3H-benzooxazol-2-one) and triethylamine (11.1 mL, 0.08 mol) in DCM (250 mL) was added trityl chloride (21.5 g, 0.08 mol). The solution was stirred at room temperature for 18 h and was then washed with distilled water (3×250 mL), brine (250 mL) and dried (MgSO$_4$), filtered and evaporated to give an off-white colored solid. The product was dissolved in refluxing EtOAc then allowed to cool to room temperature with constant stirring for several hours. The solids were collected (21.16 g) and the filtrate was concentrated until precipitation occurred, re-heated (reflux) for several hours and allowed to cool with stirring to encourage a second crystallization (7.88 g). NMR and HPLC indicated the product (29.04 g, 91%) was very clean.

Step 3: 6-(4,4,5,5-Tetramethyl-[1,3,2]dioxaborolan-2-yl)-3-trityl-3H-benzooxazol-2-one: A mixture of 6-bromo-3-trityl-benzoxazol-2-one (2.5 g, 5.48 mmol), bis(pinacolato)diboron (1.53 g, 6.03 mmol), potassium acetate (2.15 g, 21.91 mmol) and PdCl$_2$(dppf).DCM (447 mg, 0.55 mmol) in degassed, anhydrous DMSO was evacuated and then repressurized with nitrogen. This process was repeated several times to minimize the amount of oxygen in the reaction mixture. The mixture was heated at 85° C. (oil bath temperature) under a nitrogen atmosphere for 2.5 h. The reaction was diluted with DCM (700 mL) and washed twice with distilled water (300 mL each), brine (300 mL), dried (MgSO$_4$), filtered and evaporated to give a dark brown syrup.

The reaction was repeated and the product was combined with that prepared above and chromatographed on a column of silica gel, eluting with 20% Et$_2$O in heptane giving the desired product as a white powder (3.76 g, 68%). $^1$H NMR spectroscopy indicated that the product was clean besides some remaining pinacol-related material. Some less pure material (0.5 g) was also recovered and stored to be purified in later preparations.

Step 4: 4-(4-Bromofuran-2-ylmethyl)-3S-(4-fluorophenyl)-piperazine-1-carboxylic acid tert-butyl ester: 3S-(4-Fluorophenyl)-piperazine-1-carboxylic acid tert-butyl ester (1.0 g, 3.57 mmol) and 4-bromo-2-furaldehyde (0.63 g, 3.6 mmol) was dissolved in DCE (15 mL) and glacial acetic acid was added (0.23 mL, 3.55 mmol) followed by sodium tris-acetoxyborohydride (2.30 g, 10.85 mmol). The reaction was stirred overnight at room temperature. DCM (50 mL) was added and the mixture was washed with water (1×50 mL) and brine (1×50 mL) and dried over Na$_2$SO$_4$. The solvent was removed in vacuo to give an oil, which solidified on standing (1.6 g, quantitative crude yield). LC/MS: Retention time, 4.32 min; (M+H)=439.

Step 5: 1-(4-bromofuran-2-ylmethyl)-2S-(4-fluorophenyl)-piperazine-trifluoroacetate: 4-(4-Bromofuran-2-ylmethyl)-3S-(4-fluorophenyl)-piperazine-1-carboxylic acid tert-butyl ester (0.68 g, 1.55 mmol) was taken up in a mixture of 95% TFA aq. and DCM [70:30] and was stirred for 30 mins. The solvent was removed in vacuo to yield a gum (0.90 g, quantitative crude yield). LCMS: Retention time, 2.33 min; (M+H)=339.23.

Step 6: 1-(4-Bromofuran-2-ylmethyl)-2S-(4-fluorophenyl)-4-methylpiperazine: A solution of 1-(4-bromofuran-2-ylmethyl)-2S-(4-fluorophenyl)-piperazine di-trifluoroacetate (0.60 g, 1.06 mmol) in methanol (15 mL) was treated with 37% aqueous formaldehyde (2.5 mL, ~30 mmol) followed by sodium tris-acetoxyborohydride (1.25 g, 5.5 mmol). The reaction was stirred at room temperature overnight after which the solvent was removed in vacuo to give a gum. Water (20 mL) was added and adjusted to pH 11 with 10M NaOH aq. The mixture was extracted with DCM (4×20 mL) and the combined DCM layers were washed with brine and dried over Na$_2$SO$_4$. Solvent removal in vacuo afforded a thick brown oil (0.35 g, 94%). This compound was purified via flash silica gel chromatography using DCM:MeOH:AcOH:water (240:15:3:2) as eluent. LC/MS: Retention time, 2.28 min; (M+H)=353.

Step 7: 6-{5-[2S-(4-Fluorophenyl)-4-methylpiperazine-1-ylmethyl]-furan-3-yl}-3-trityl-3H-benzoxazol-2-one: 1-(4-Bromofuran-2-ylmethyl)-2S-(4-fluorophenyl)-4-methylpiperazine (0.164 g, 0.33 mmol) and 6-(4,4,5,5-tetramethyl-[1,3,2]dioxaborolan-2-yl)-3-trityl-3H-benzooxazol-2-one (0.105 g, 0.30 mmol) were dissolved in dioxane (8 mL) and 2M Cs$_2$CO$_3$ aq. (0.65 mL, 1.3 mmol) was added. The mixture was de-gassed and nitrogen was introduced (three times) when PdCl$_2$(dppf).DCM (0.027 g, 0.03 mmol) was added. After a further de-gassing, the reaction was heated at 100° C. for 4 hours when the reaction was complete as monitored by T.L.C. DCM (20 mL) was added to the mixture and was washed with water (3×20 mL) and brine (1×20 mL). The organic layer was dried over MgSO$_4$ and the solvent removed in vacuo. Chromatography using DCM:MeOH:AcOH:water (240:15:3:2) as eluent gave 0.11 g of the product (68%).

LC/MS: Retention time, 3.13 min; (M+H)=650

Step 8: 6-{5-[2S-(4-Fluorophenyl)-4-methylpiperazine-1-ylmethyl]-furan-3-yl}-3H-benzoxazol-2-one: 6-{5-[2S-(4-Fluorophenyl)-4-methylpiperazine-1-ylmethyl]-furan-3-yl}-3-trityl-3H-benzoxazol-2-one (0.33 g, 0.51 mmol) was taken up in 90% TFA aq. (20 mL) and stirred at room temperature for 2 hours. The solvent was removed in vacuo and co-evaporation of residual TFA was achieved using water (3×2 mL) to afford a brown solid. Chromatography using DCM:MeOH:AcOH:water (180:20:3:2) as eluent provided 0.15 g of the product (73%). LC/MS (long run): Retention time, 4.39 min; (M+H)=408.

$^1$H NMR (400 MHz, methanol-D$_4$) δ ppm: 2.73 (td, J=12.58, 2.75 Hz, 1 H) 2.83 (s, 3 H) 3.04 (t, J=11.76 Hz, 1 H) 3.16-3.26 (m, 2 H) 3.33-3.42 (m, 2 H) 3.50 (dd, J=12.09, 1.98 Hz, 1 H) 3.65-3.71 (m, 2 H) 6.54 (s, 1 H) 7.07 (d, J=8.13 Hz, 1 H) 7.20 (t, J=8.79 Hz, 2 H) 7.33 (dd, J=8.13, 1.54 Hz, 1 H) 7.39 (d, J=1.54 Hz, 1 H) 7.56 (dd, J=8.46, 5.39 Hz, 2 H) 7.83 (d, J=0.88 Hz, 1 H).

Example 5

Study of the Effects of a Combination of an Antagonist of the GABA Receptors and an Inhibitor of the 5HT2A Receptors in Improving the Quality of Sleep For this study, four groups of male Sprague-Dawley rats are used, each group comprises 5 to 9 rats.

Group A receives 0.3 mg/kg i.p. Example 4 (intraperitoneally)

Group B receives 3 mg/kg p.o. zolpidem (orally, hemitartarate)

Group C receives the combination—0.3 mg/kg i.p. Example 4 and 3 mg/kg p.o. zolpidem hemitartarate, the two compounds are administered in 5-minute intervals orally.

Finally, group D receives 10 mg/kg p.o. zolpidem (orally, hemitartarate). The data are recorded on day 0 (reference date) when animals receive only a carrier (distilled water and methylcellulose) and on day 1 when animals receive the active principle. The data are recorded for 6 hours each day, active principles are administered 15 minutes after the beginning of the record.

The synergistic effects of the combination is measured by the decrease in the waking-up time (total waking-up time during the 6 hours of recordation), increase in the non-rapid eye movement (NREM) duration (total duration of NREM sleep during the 6 hours of recordation), and general decrease in the number of NREM sleep periods. Thus the combination of the invention enhances sleep quality in a patient.

Example 6

Preparation of a Capsule Containing Example 4 and Zolpidem

A capsule is prepared containing, in the form of a small size tablet, 1.18 mg Example 4 as sleep aid and 6.22 mg zolpidem hemitartarate as a short-acting hypnotic agent. The tablet contains the ingredients as listed in Table I below.

TABLE I

| Ingredient | Percent by Weight |
| --- | --- |
| Micronized Example 4 | 2.36 |
| Monohydrated lactose[1] | 87.14 |
| Gelatinized Starch[2] | 8 |
| Sodium croscarmellose[3] | 2 |
| Magnesium stearate | 0.5 |

[1]Pharmatose DMV
[2]Starch 1500
[3]Ac-di-sol (FMC)

First the mixture of Example 4, monohydrated lactose, Gelatinized Starch, sodium croscaramellose and magnesium stearate is prepared. The mixture is then placed in biconic mixer for thirty minutes. The homogenous mixture is then compressed, by using a normal rotary compressed machine, in the form of 50 mg tablet.

The zolpidem hemitartarate tablet is prepared using the ingredients shown in Table II below.

TABLE II

| Ingredient | Percent by Weight |
| --- | --- |
| Zolpidem hemitartarate | 10.37 |
| Lactose | 83.73 |
| Microcrystalline cellulose[4] | 10.0 |
| Hydroxypropylmethylcellulose 606[5] | 2.1 |
| Sodium carboxymethylcellulose | 3.2 |
| Magnesium stearate | 0.6 |

[4]Avicel (FMC)
[5]Pharmacoat 606 (Shin-Etsu)

The Zolpidem hemitartarate, lactose, microcrystalline cellulose, hydroxypropylmethylcellulose and sodium carboxymethylcellulose are mixed together, and then are granulated with water. The granulate is then dried and calibrated. The granulate is then mixed with the magnesium stearate and compressed in a mass of 60 mg per tablet, by using rotary compressed machine.

Then, tablets with a dose of 1 mg of Example 4 and 6.42 mg of zolpidem hemitartarate are introduced in a hard gelatin capsule.

The capsules dissolution profiles can be measured by using a II device of the US Pharmacopoeia, with two dissolution medium:

900 ml of hydrochloric acid 0.01 M and 900 ml of potassium phosphate buffer 0.05 M at pH 6:8, maintained at 37+/−0.5° C., with stirring (50 t.p. min.)

Example 7

Preparation of a Capsule Containing an Immediate-release Example 4 Tablet and a Delayed Release Zolpidem Tablet The immediate release Example 4 tablets are prepared according to the process described in Example 6 above.

The delayed release zolpidem hemitartarate tablet is prepared according to the method described in Example 6 above in order to obtain a tablet having the composition indicated in Table III below.

TABLE III

| Ingredients | Percent by Weight |
| --- | --- |
| Zolpidem hemitartarate | 12.4 |
| Monohydrated lactose[6] | 33.4 |
| Hydroxypropylmethylcellulose 4000 mPa · s[7] | 25.0 |
| Microcrystalline cellulose[8] | 20.0 |
| Hydrogen potassium tartrate | 8.0 |
| Magnesium stearate | 1.0 |
| Colloidal anhydrous silica | 0.2 |
| Purified water | q.s. |

[6]Pharmatose (DMV)
[7]Metolose 90SH4000 (Shin-Etsu)
[8]Avicel PH 102 (FMC)

The same humid granulation and compression methods are used, such as those described for the zolpidem hemitartarate in Example 6 above. Capsules are prepared containing one or more of the 50 mg delayed release tablets containing 5 mg of zolpidem base (corresponding to 6.22 mg of zolpidem hemitartarate) and one more of the 50 mg immediate-release tablets containing 1 mg of Example 4.

The in vitro dissolution profiles of the capsules prepared like this can be established by using the method described in Example 6 above Example 8

Preparation of a Capsule Comprising a Mixture of Immediate-release Example 4 Pellets and of Immediate-release Zolpidem Pellets A suspension of 50 g of Example 4 and of 100 g of povidone (Pladone K29/32, BASF) in 670 g of ethanol is prepared. 750 g of that suspension are then pulverized on 1060 g of microgranules of 16-18 mesh size, by using a fluidized bed dryer. Then, a suspension of 62.2 g of zolpidem tartrate (corresponding to 50g of zolpidem base) and of 100 g of povidone (Pladone K29/32, BASF) in 670 g of ethanol is prepared. 750 g of that suspension are then pulverized on 1060 g of microgranules of 16-18 mesh size, by using a fluidized bed dryer. A mixture of the two pellets is prepared, with a ratio of 1 part in weight of Example 4 for 5 part of zolpidem tartrate. This mixture is put in a hard gelatin capsule having a total quantity of 1 mg of Example 4 and 5 mg of zolpidem in the base form (corresponding to 6.22 mg of zolpidem tartrate). The quantity of each of the pellets can be modified in order to adjust the dose.

The in vitro dissolution profiles of the capsules prepared like this can be established by using the method described in Example 6 above.

Example 9

Preparation of a Capsule Comprising a Mixture of Immediate-release Example 4 Pellets and of Delayed Release Zolpidem Pellets The immediate-release Example 4 pellets are prepared according to the method described in Example 8 above. Similarly, Zolpidem hemitartarate pellets are prepared such as described above in Example 6.

A solution comprising 25 g of methacrylate copolymer (Eudragit TM RL 100, Rohm Pharma), 143 g of methacrylate copolymer (Eudragit TM RS 100, Rohm Pharma) and 18.7 g of ethyl citrate (Eudrafex TM, Rohm Pharma) is prepared in a 1180 g isopropanol/acetone 60:40 (wt/wt) mixture. The zolpidem hemitartarate pellets are coated with this mixture of polymers, by pulverization in a fluidized bed dryer, the final quantity of coating represents 20% by weight of the non coated pellet mass. After saturation of pellets at 35° C. for 24 hours, a mixture of coated zolpidem hemitartarate pellets and Example 4 pellets is prepared, in the proportion of 1:2 (Example 4/zolpidem), and this mixture is put in gelatin capsules in order to give a quantity per capsule corresponding to 5 mg of Example 4 and 10 mg of zolpidem base.

The in vitro dissolution profiles of the capsules prepared like this can be established by using the method described in Example 6 above.

Example 10

Preparation of a Tablet Comprising Immediate-release Example 4 Pellets and Immediate-release Zolpidem Pellets Example 4 and zolpidem hemitartarate pellets are prepared according to the method described in Example 8 above.

A mixture by weight of the two pellets is prepared in a ratio of 1 part of Example 4 for 2 parts of zolpidem hemitartarate, and 0.1% of magnesium stearate is added. The mixture is then placed in a biconical mixer for 30 minutes.

The homogenous mixture is then compressed by using a conventional rotary compression machine, in order to give a tablet having 5 mg of Example 4 and 12.44 mg of zolpidem hemitartarate (corresponding to 10 g of zolpidem in the base form). The in vitro dissolution profiles of the capsules prepared like this can be established by using the method described in Example 6 above.

Example 11

Preparation of a Tablet Comprising Immediate-release Example 4 Pellets and Delayed-release Zolpidem Pellets The immediate-release Example 4 pellets are prepared according to the method described in Example 8 and the delayed release zolpidem hemitartarate pellets according to the method described in Example 9.

A mixture of the two pellets is prepared in a ratio of 2 parts of Example 4 and 6 parts of zolpidem hemitartarate, and 0.2% of magnesium stearyl fumarate are added. The mixture is then transferred into a biconical mixer for 30 minutes. The homogenous mixture is then compressed by using a conventional rotary compression machine, in order to give a total quantity of 4 mg of Example 4 and 14.93 mg of zolpidem hemitartarate (corresponding to 12 g of zolpidem base). The in vitro dissolution profiles of the capsules prepared like this can be established by using the method described in Example 6 above.

Example 12

Preparation of a Delayed Release Enteric Tablet Comprising Immediate-release Example 4 Pellets and Immediate-release Zolpidem Pellets Tablets are prepared comprising both Example 4 and zolpidem hemitartarate according to the process described in Example 10. Tablets are then coated according to the process known by the person skilled in the art and described hereafter.

A solution of 46 g of methacrylate copolymer (Eudragit TM RL100, Rohm Pharma), 295 g of methacrylate copolymer (Eudragit TM RS 100, Rohm Pharma) and 40 g of ethyl citrate (Eudrafex TM, Rohm Pharma) in 2280 g of a mixture isopropanol/acetone 65:35 (wt/wt) is prepared.

The tablets comprising 3.2 mg of Example 4 and 12.44 mg of zolpidem hemitartarate are coated with polymeric mixture, by pulverization in a coating pan, the final quantity of the coating represents 5 to 10% in weight of the pellet mass without coating.

Example 13

Preparation of a Bilayer Tablet Comprising an Immediate-release Example 4 Layer and an Immediate-release Zolpidem Layer Granulates A are prepared by dry mixture and granulates B by wet mixture according to Example 6 using the compositions as listed in Table IV below.

TABLE IV

| Ingredients | Percent by Weight |
| --- | --- |
| Granulates A | |
| Example 4 | 2.95 |
| Dry monohydrated lactose[9] | 82.71 |
| Pregelatinized Starch[10] | 8.00 |
| Croscarmellose[11] | 2.00 |
| Sodium carboxymethylcellulose[12] | 3.80 |
| Magnesium stearate[13] | 0.54 |
| Granulates B | |
| Zolpidem hemitartarate | 6.22 |
| Monohydrated lactose[9] | 73.88 |
| Microcrystalline cellulose[14] | 14.0 |
| Hydroxypropylmethylcellulose 606[15] | 2.1 |
| Sodium carboxymethylcellulose[12] | 3.2 |
| Magnesium stearate[13] | 0.6 |

[9]Pharmatose (DMV)
[10]Starch 1500 (Colorcon)
[11]Ac-di-sol (FMC)
[12]Blanose (Aqualon)
[13]Brentag AG
[14]Avicel PH 102 (FMC)
[15]Pharmacoat 606 (Shin-Etsu)

The mixtures are then compressed into a bilayer tablet by using an alternative compression machine, the first immediate-release layer with a 200 mg mass of granulate A comprising 5 mg of Example 4 and the second immediate-release layer with a 200 mg mass of granulate B comprising 12.44 mg of zolpidem hemitartarate (corresponding to 10 mg of zolpidem base).

The in vitro dissolution profiles of the capsules prepared like this can be established by using the method described in Example 6 above.

Example 14

Preparation of a Bilayer Tablet Comprising an Immediate-release Example 4 Layer and a Delayed Release Zolpidem Layer Granulates C are prepared by dry mixture and granulates D by wet mixture according to Example 6 using the compositions as listed in Table V below.

TABLE V

| Ingredients | Percent by Weight |
| --- | --- |
| Granulates C | |
| Example 4 | 2.95 |
| Dry monohydrated lactose[16] | 84.00 |
| Pregelatinized Starch[17] | 7.70 |
| Croscarmellose[18] | 2.00 |
| Sodium carboxymethylcellulose[19] | 3.4 |
| Magnesium stearate[20] | 0.54 |
| Granulates D | |
| Zolpidem hemitartarate | 7.75 |
| Lactose 150 mesh[16] | 37.85 |
| Microcrystalline cellulose[21] | 20.0 |
| Tartaric acid (23) | 8.4 |
| Hydroxypropylmethylcellulose[22] | 25.0 |
| Magnesium stearate[23] | 1.0 |

[16]Pharmatose (DMV)
[17]Starch 1500 (Colorcon)
[18]Ac-di-sol (FMC)
[19]Blanose (Aqualon)
[20]Brentag AG
[21]Avicel PH 102 (FMC)
[22]Metolose 90SH4000 (Shin-Etsu)
[23]Brentag AG The mixtures are then compressed into a bilayer tablet by using an alternative compression machine, the first immediate-release layer with a 150 mg mass of granulate C comprising 3.75 mg of Example 4 and the second delayed release layer with a 200 mg mass of granulate D comprising 15.50 mg of zolpidem hemitartarate (corresponding to 12.45 mg of zolpidem base).

The in vitro dissolution profiles of the capsules prepared like this can be established by using the method described in Example 5 above.

Example 15

Preparation of a Three Layers Tablet Comprising One Immediate-release Example 4, One Inactive Layer and a Third Delayed Release Zolpidem Layer Granulates E and F are prepared by dry mixture and granulates G by wet mixture according to Example 6 and using the compositions listed in table VI below.

TABLE VI

| Ingredients | Percent by Weight |
| --- | --- |
| Granulates E (immediate release) | |
| Example 4 | 2.36 |
| Dry monohydrated lactose[24] | 87.14 |
| Pregelatinized Starch[25] | 8.0 |
| Croscarmellose[26] | 2.0 |
| Sodium carboxymethylcellulose[27] | 3.8 |
| Magnesium stearate[28] | 0.54 |
| Granulates F (inactive) | |
| Dry monohydrated lactose[24] | 60.0 |
| Microcrystalline cellulose[29] | 24.0 |
| Tartaric acid[30] | 10.0 |
| Hydroxyethylcellulose | 5.0 |
| Magnesium stearate[28] | 1.0 |
| Granulates G (delayed release) | |
| Zolpidem hemitartarate | 5.0 |
| Lactose 200 mesh[24] | 67.7 |
| Microcrystalline cellulose[29] | 20.0 |

TABLE VI-continued

| Ingredients | Percent by Weight |
| --- | --- |
| Hydroxypropylmethylcellulose 606[31] | 2.5 |
| Sodium carboxymethylcellulose[27] | 3.8 |
| Magnesium stearate[28] | 1.0 |

[24]Pharmatose (DMV)
[25]Starch 1500 (Colorcon)
[26]Ac-di-sol (FMC)
[27]Blanose (Aqualon)
[28]Brentag AG
[29]Avicel PH 102 (FMC)
[30]Brentag AG
[31]Pharmacoat (Shin-Etsu)

The mixtures are compressed, according to Example 13, into a three layers tablet, a 125 mg mass external layer of granulate E comprising 2.5 mg of Example 4, a 125 mg intermediary layer of granulate F and a third 300 mg mass external layer of granulate G comprising 15 mg of zolpidem hemitartarate (corresponding to 12.06 mg of zolpidem base).

Example 16

Preparation of a Dry Coated Tablet Comprising an Internal Core of Zolpidem and an External Coating of Example 4

Granulates are prepared according to Example 6, and based on the compositions listed in table VII below.

TABLE VII

| Ingredients | Percent by Weight |
| --- | --- |
| Internal core (delayed release) | |
| Zolpidem hemitartarate | 15.55 |
| Monohydrated lactose 200 mesh[32] | 36.05 |
| Microcrystalline cellulose[33] | 18.0 |
| Hydroxypropylmethylcellulose[34] | 21.0 |
| Tartaric acid[35] | 8.4 |
| Magnesium stearate[35] | 1.0 |
| External coating (immediate release) | |
| Example 4 | 1.96 |
| Monohydrated lactose 150 mesh[32] | 52.00 |
| Microcrystalline cellulose[33] | 39.84 |
| Hydroxypropylmethylcellulose 606[34] | 2.2 |
| Sodium carboxymethylcellulose[36] | 3.0 |
| Magnesium stearate[35] | 1.0 |

[32]Pharmatose (DMV)
[33]Avicel PH 102 (FMC)
[34]Metolose 90SH4000 (Shin-Etsu)
[35]Brentag AG
[36]Blanose (Aqualon)

The granulate forming the internal core is compressed, by using an alternative compression machine, in little tablets, before performing the dry coating operation with the second layer. This operation produces 80 mg delayed release tablets, containing 12.44 mg of zolpidem hemitartarate (corresponding to 10 mg of zolpidem base).

The granulate forming the external coating layer is compressed, by using an alternative compression machine that allows the little internal core tablets. The external layer has a mass of 301 mg and contains 5 mg of Example 4.

According to another of its aspects, the object of the invention is to use at least one long-acting hypnotic agent and/or a sleep aid in combination with at least one short-acting hypnotic agent, for the preparation of a medication aimed to prevent and/or to treat the sleep disorders.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A combination comprising at least one short acting hypnotic agent selected from the group consisting of zolpidem, zopiclone, eszopiclone, zaleplon, ramelteon, triazolam, etizolam, brotizolam and indiplon, and a compound defined by formula I, an enantiomer, a stereoisomer, a tautomer or a pharmaceutically acceptable salt thereof:

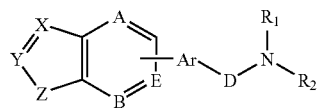
(I)

wherein:
X=Y denotes either a single or double bond between X and Y;
X is CR, N, or O;
Y is CR, CHR, CO, or N;
Z is NR;
A, B and E are the same or different and independently from each other are CR;
D is $CH_2$;
Ar is substituted or unsubstituted phenyl or furan;
each R is independently chosen from hydrogen, halogen, CN, or $C_{1-4}$alkyl $C_{1-4}$alkoxy, $C_{1-4}$alkenyl,
$R_1$ and $R_2$ are the same or different and selected independently of each other from substituted or unsubstituted phenyl, benzyl, benzoyl, pyrrolidinylmethyl, and $diC_{1-4}$ alkylaminoalkyl; or
$R_1$ and $R_2$ taken together with the nitrogen atom to which they are attached form an unsubstituted or at least mono-substituted piperazine; and wherein
the substituents are selected from the group consisting of substituted or unsubstituted phenyl, $C_{3-8}$cycloalkyl, $C_{1-4}$alkyl, $C_{1-4}$alkoxy, $C_{1-4}$alkenyl, fluoroalkyl of the formula $C_nH_xF_y$, and fluoroalkoxy of the formula $OC_nH_xF_y$, wherein n is an integer from 1 to 4, x is an integer from 0 to 8, y is an integer from 1 to 9 and sum of x and y is 2n+1.

2. The combination as set forth in claim 1, wherein the short-acting hypnotic agent is present in a galenic form adapted for an immediate or delayed release, and a compound of formula (I) is present in a galenic form adapted for an immediate release.

3. The combination as set forth in claim 1, wherein the short-acting hypnotic agent is selected from the group consisting of zolpidem, zopiclone, eszopiclone, zaleplon, ramelteon, and indiplon.

4. The combination as set forth in claim 1, wherein the short acting hypnotic agent is zolpidem or a pharmaceutically acceptable salt thereof which is in combination with a compound of formula (I).

5. A pharmaceutical composition comprising at least one short acting hypnotic agent from the group consisting of zolpidem, zopiclone, eszopiclone, zaleplon, ramelteon, triazolam, etizolam, brotizolam and indiplon, and a compound defined by formula I, an enantiomer, a stereoisomer, a tautomer or a pharmaceutically acceptable salt thereof:

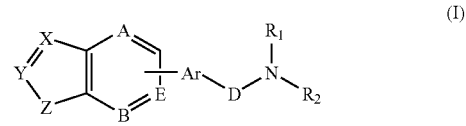
(I)

wherein:
X=Y denotes either a single or double bond between X and Y;
X is CR, N, or O;
Y is CR, CHR, CO, or N;
Z is NR;
A, B and E are the same or different and independently from each other are CR;
D is $CH_2$;
Ar is substituted or unsubstituted phenyl or furan;
each R is independently chosen from hydrogen, halogen, CN, $C_{1-4}$alkyl, $C_{1-4}$alkoxy, $C_{1-4}$alkenyl;
$R_1$ and $R_2$ are the same or different and selected independently of each other from substituted or unsubstituted phenyl, benzyl, benzoyl, pyrrolidinylmethyl, and $diC_{1-4}$ alkylaminoalkyl; or
$R_1$ and $R_2$ taken together with the nitrogen atom to which they are attached form an unsubstituted or at least mono-substituted piperazine; and wherein
the substituents are selected from the group consisting of substituted or unsubstituted phenyl, $C_{3-8}$cycloalkyl, $C_{1-4}$alkyl, $C_{1-4}$alkoxy, or $C_{1-4}$alkenyl, fluoroalkyl of the formula $C_nH_xF_y$, and fluoroalkoxy of the formula $OC_nH_xF_y$, wherein n is an integer from 1 to 4, x is an integer from 0 to 8, y is an integer from 1 to 9 and sum of x and y is 2n+1;
in combination with one or more pharmaceutically acceptable diluent, excipient or a carrier.

6. The composition as set forth in claim 5, wherein the short-acting hypnotic agent is present in a galenic form adapted for an immediate or delayed release, and a compound of formula (I) is present in a galenic form adapted for an immediate release.

7. The composition as set forth in claim 5, wherein the short-acting hypnotic agent is selected from the group consisting of zolpidem, zopiclone, eszopiclone, zaleplon, ramelteon and indiplon.

8. The composition as set forth in claim 5, wherein the short-acting hypnotic agent is zolpidem or a pharmaceutically acceptable salt thereof which is in combination with a compound of formula (I).

9. The composition as set forth in claim 5, wherein the short-acting hypnotic agent and a compound of formula (I) are released immediately.

10. The composition as set forth in claim 5, which is formulated a tablet containing immediate-release pellets of the short-acting hypnotic agent and a compound of formula (I).

11. The composition as set forth in claim 5, which is formulated a delayed-release enteric coated tablet comprising immediate-release pellets of a compound of formula (I) and immediate-release pellets of the short-acting hypnotic agent.

* * * * *